(12) United States Patent
Popowski et al.

(10) Patent No.: US 8,734,314 B2
(45) Date of Patent: May 27, 2014

(54) METHOD AND KIT FOR DELIVERY OF BRACHYTHERAPY TO A SUBJECT

(75) Inventors: Youri Popowski, Genève (CH); Erwin Berger, Stettfurt (CH)

(73) Assignee: Acrostak Corp., Winterthur (CH)

( * ) Notice: Subject to any disclaimer, the term of this patent is extended or adjusted under 35 U.S.C. 154(b) by 996 days.

(21) Appl. No.: 12/733,350

(22) PCT Filed: Aug. 26, 2008

(86) PCT No.: PCT/EP2008/061139
§ 371 (c)(1),
(2), (4) Date: Feb. 23, 2010

(87) PCT Pub. No.: WO2009/027394
PCT Pub. Date: Mar. 5, 2009

(65) Prior Publication Data
US 2010/0185173 A1    Jul. 22, 2010

Related U.S. Application Data

(60) Provisional application No. 60/966,601, filed on Aug. 29, 2007.

(30) Foreign Application Priority Data

Aug. 29, 2007    (EP) .................................... 07115233

(51) Int. Cl.
*A61N 5/00*    (2006.01)
(52) U.S. Cl.
USPC .............................................. 600/3; 604/500
(58) Field of Classification Search
USPC .................................. 600/1–8; 604/540–544
See application file for complete search history.

(56) References Cited

U.S. PATENT DOCUMENTS

| 6,099,454 A | 8/2000 | Hastings et al. |
| 6,251,060 B1 | 6/2001 | Hooft et al. |

(Continued)

FOREIGN PATENT DOCUMENTS

| EP | 1 666 083 A | 6/2006 |
| WO | WO 02/053230 A | 7/2002 |
| WO | WO 2008/048521 A | 4/2008 |

OTHER PUBLICATIONS

The Search Report for PCT Application No. PCT/EP2008/061139.

(Continued)

*Primary Examiner* — Christine Matthews
(74) *Attorney, Agent, or Firm* — Amster, Rothstein & Ebenstein LLP

(57) ABSTRACT

The present invention provides a kit for delivering catheter brachytherapy to a subject comprising a medical balloon catheter (1) having a proximal (2) and distal (3) end, comprising a elongated catheter tube (5) with an inflation lumen (21) extending therewithin and at least one inflatable balloon (4, 4') towards the distal end (3) in fluid communication with the catheter tube (5) inflation lumen (21), the catheter tube (5) configured to unfold from a kinked condition permitting the inflation lumen (21) to slidably receive a removable inner tube (6), the inflation lumen (21) configured to carry inflation fluid to the least one inflatable balloon (4, 4') in the presence of the removable inner tube (6); and a removable inner tube (6) having an elongated body, an open (9) proximal end (7), a closed (10) distal end (8), and a source wire lumen (22) extending therewithin, wherein the removable inner tube (6) is configured for insertion into and removal from at least part of the length of the inflation lumen (21), and the source wire lumen (22) configured to receive a source wire (19) bearing a therapeutic radiation source (20). It also provides a method for delivering catheter brachytherapy to a subject.

28 Claims, 8 Drawing Sheets

(56) References Cited

U.S. PATENT DOCUMENTS

| | | |
|---|---|---|
| 6,579,221 B1 | 6/2003 | Peterson |
| 6,770,058 B1 | 8/2004 | Liprie |
| 7,662,145 B2 * | 2/2010 | Bolmsjo et al. ............... 604/544 |
| 2002/0165424 A1 * | 11/2002 | Forman .............................. 600/3 |
| 2005/0080313 A1 | 4/2005 | Stewart et al. |
| 2006/0173235 A1 | 8/2006 | Lim et al. |
| 2006/0205992 A1 | 9/2006 | Lubock et al. |
| 2007/0049786 A1 | 3/2007 | Edmundson |

OTHER PUBLICATIONS

The Search Report for PCT Application No. PCT/EP2008/061139, Apr. 12, 2008.

* cited by examiner

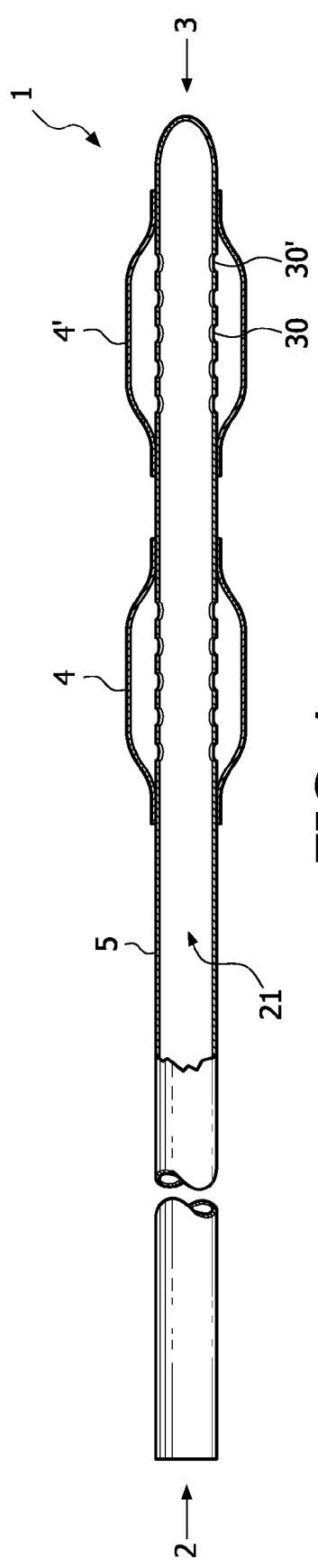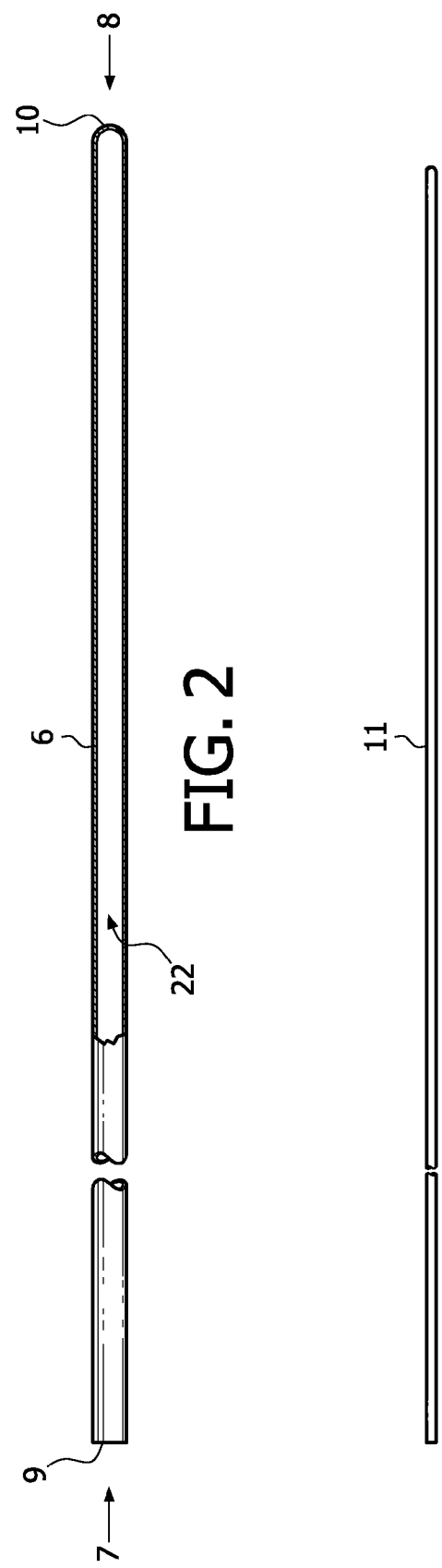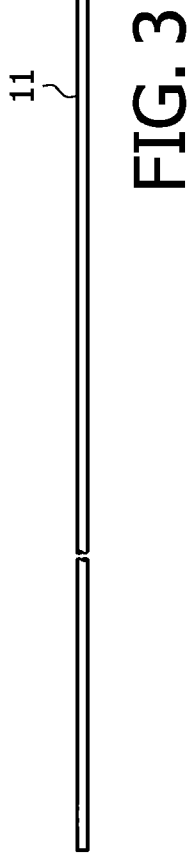

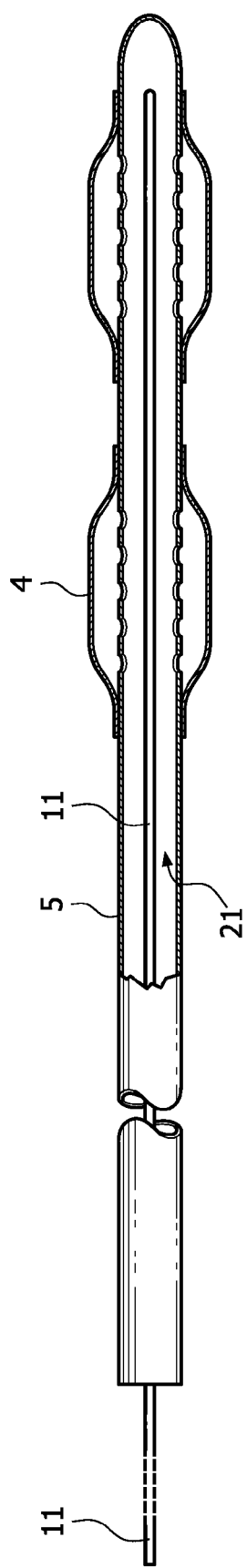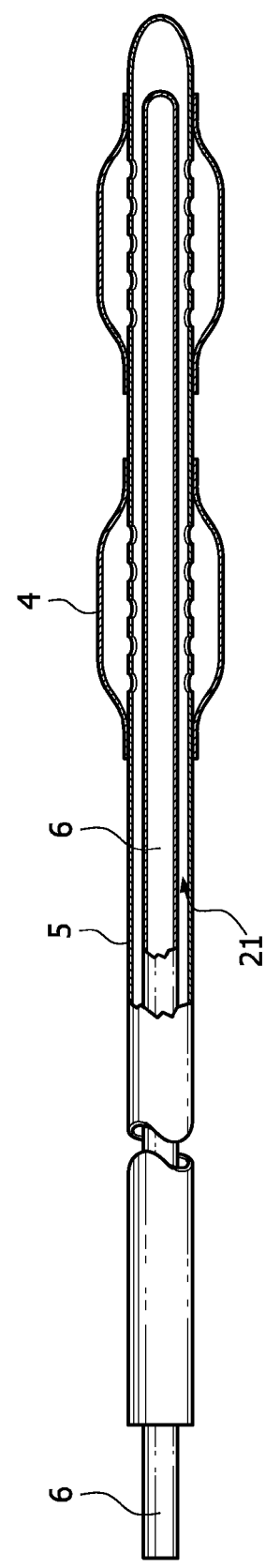

METHOD AND KIT FOR DELIVERY OF BRACHYTHERAPY TO A SUBJECT

This is a U.S. national phase of PCT Application No. PCT/EP2008/061139, filed Aug. 26, 2008, which claims the benefit of U.S. Provisional Application No. 60/966,601, filed Aug. 29, 2007 and European Application No. 07115233.4, filed Aug. 29, 2007.

FIELD OF THE INVENTION

The present invention pertains to the field of catheter brachytherapy of a subject. More particularly, the present invention pertains to a brachytherapy catheter whose rigidity can be modified depending on the stage of treatment.

BACKGROUND OF THE INVENTION

Catheter brachytherapy provides internal radiotherapy treatment to a subject, whereby a radioactive source is advanced along a catheter which tip is inserted close to a region of treatment. It is commonly used to treat oesophageal and uterine cancers, and head and neck cancers. Catheter brachytherapy is well known in the art. Clinical studies indicate that brachytherapy is an effective treatment for reducing size and rate of growth of cancers, in palliative care as well as in curative indications.

For some indications, such as in esophageal cancer, catheter brachytherapy entails that a skilled practitioner introduces a guidewire into the subject using a visualizing instrument such as an endoscope, to ensure the correct route and position of the guidewire. Once the guidewire is positioned, a catheter is introduced using the guidewire, and appropriately positioned into the subject. A radiation source attached to the end of a source wire is then advanced through the catheter so that the radiation source reaches the treatment site and can deliver an effective dose of radiation. After the radiation treatment, the radiation source is removed. The catheter cannot remain in place for subsequent treatments and is thus removed. The insertion procedure must be repeated again for each treatment session.

The particular procedure is highly traumatic for the subject, as it can take some time to position the catheter, and also to avoid infection in the case of incision entry. When treating esophageal cancer, the catheter is passed though the oral cavity and throat; it typically has a large diameter, producing severe discomfort owing to a choking and/or gagging sensation. Typically the subject must be sedated. In addition, the catheter must remain in place throughout the course of the treatment during which time the patient is in constant distress. Furthermore, brachytherapy sometimes has to be fractionated i.e. repeated several times in subsequent visits, which fractionated treatment is more efficaceaous and less toxic. This means that this painful procedure has to be imposed on a patient several times. There is a limit to what a patient can endure; therefore, fractionated treatment must be restricted, and, can be considered only to boost the treated area after external radiotherapy. There is a need to develop a way to perform user-friendly, brachytherapy that is less traumatic for the patient.

The present invention provides a new method and kit for performing catheter brachytherapy which overcomes the problem of patient discomfort and stress during a course of treatment, and facilitates fractionated treatment.

FIGURE LEGENDS

FIG. 1 depicts a cross-sectional view of a medical balloon catheter comprising an elongated catheter tube with an inflation lumen and two inflatable balloons in fluid communication with the inflation lumen.

FIG. 2 depicts a cross-sectional view of a removable inner tube having an elongated body, and open proximal, a closed distal end and a source wire lumen extending therewithin.

FIG. 3 depicts a schematic view of a pusher wire configured for insertion into and removal from the inflation lumen to provide rigidity to the catheter tube during insertion into a subject via a nasopharyngeal route.

FIG. 4 shows a view of the pusher wire inserted into the inflation lumen of the elongated catheter tube.

FIG. 5 shows a view of the removable inner tube inserted into the inflation lumen of the elongated catheter tube.

Figure 6:
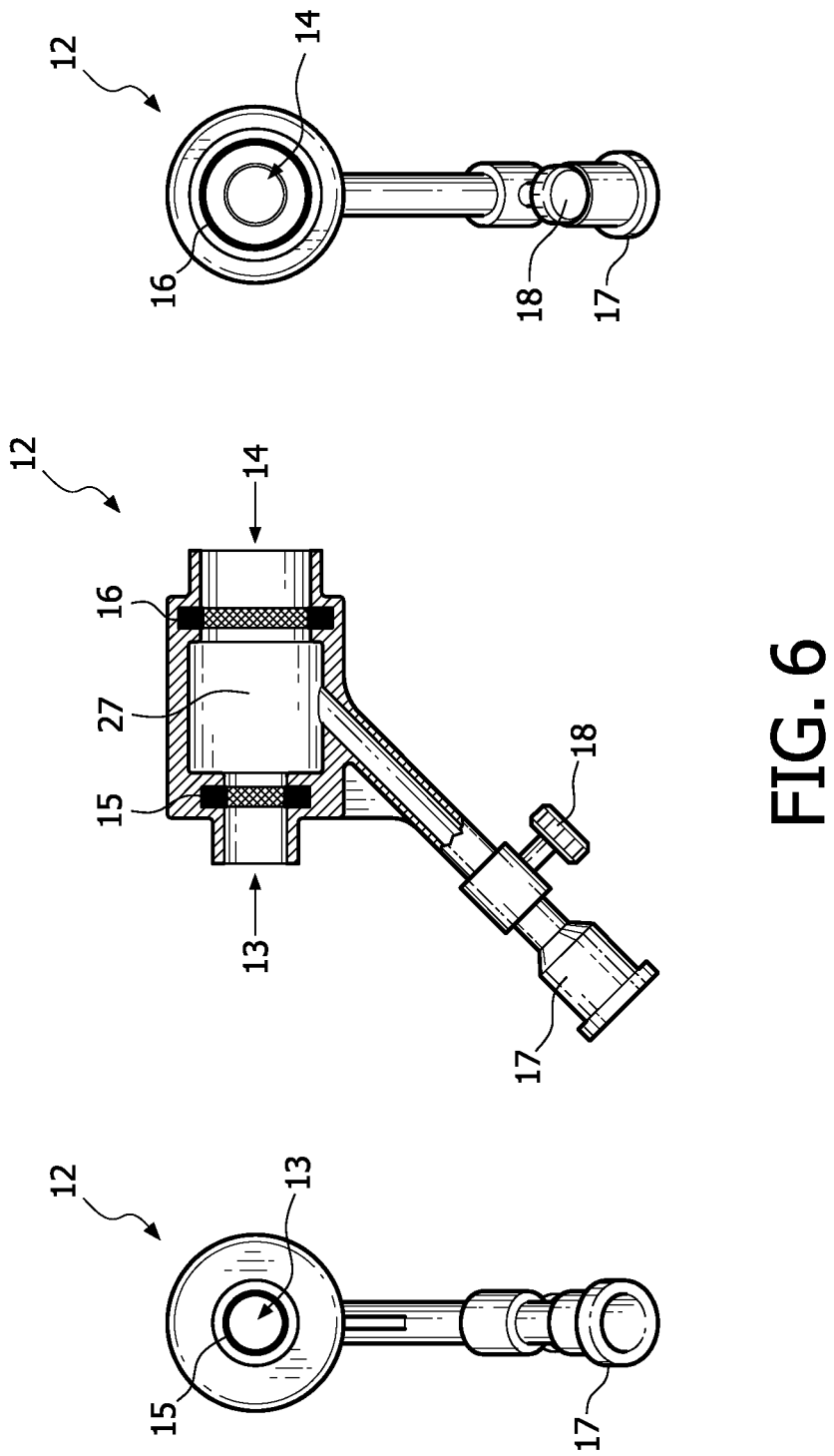

FIG. 6: shows a cross-sectional view of an inflation coupling configured to couple the proximal end of the catheter tube to an inflation pump to allow inflation of the balloons.

Figure 7:
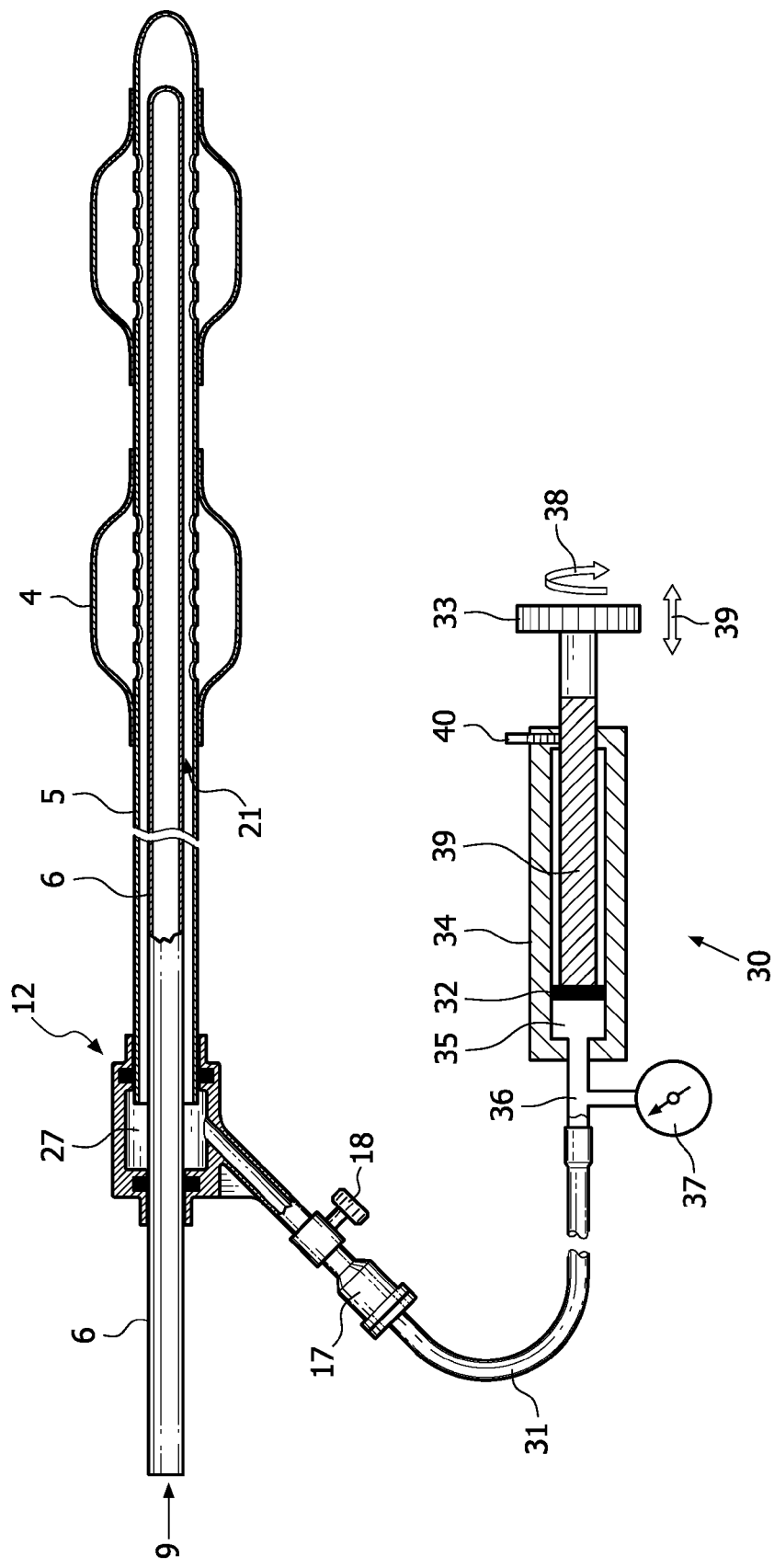

FIG. 7: shows a cross-sectional view of an inflation coupling attached the proximal end of the catheter tube, sealing the inflation lumen while allowing access to the open end of the removable inner tube. Attached to the inflation coupling is a pump. The balloons are inflated.

Figure 8:
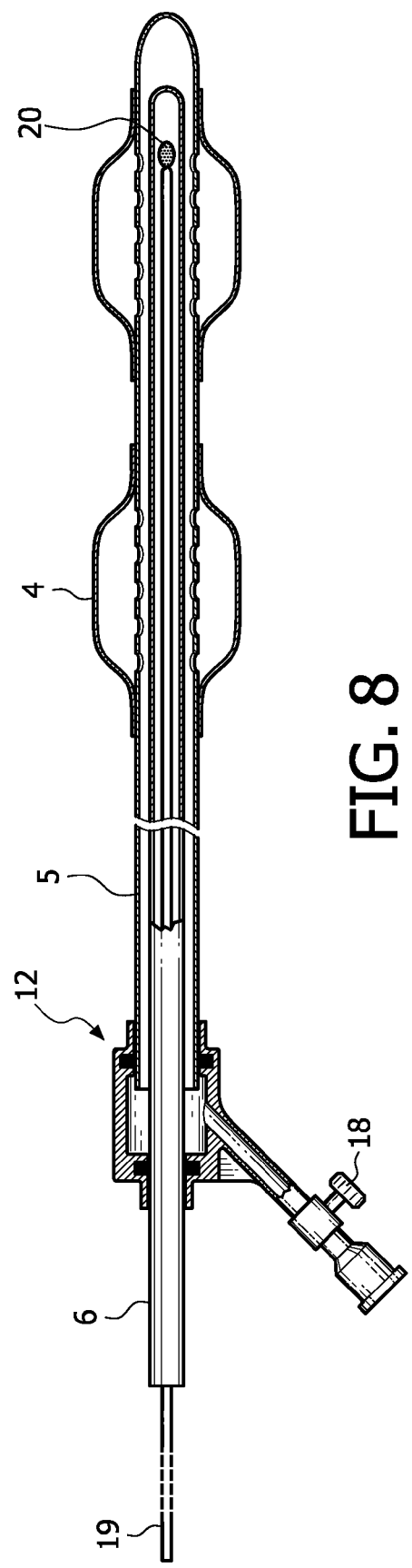

FIG. 8: shows a cross-sectional view of an inflation coupling attached the proximal end of the catheter tube and a source wire inserted into the source wire lumen of the removable inner tube. The balloons are inflated.

Figure 9:
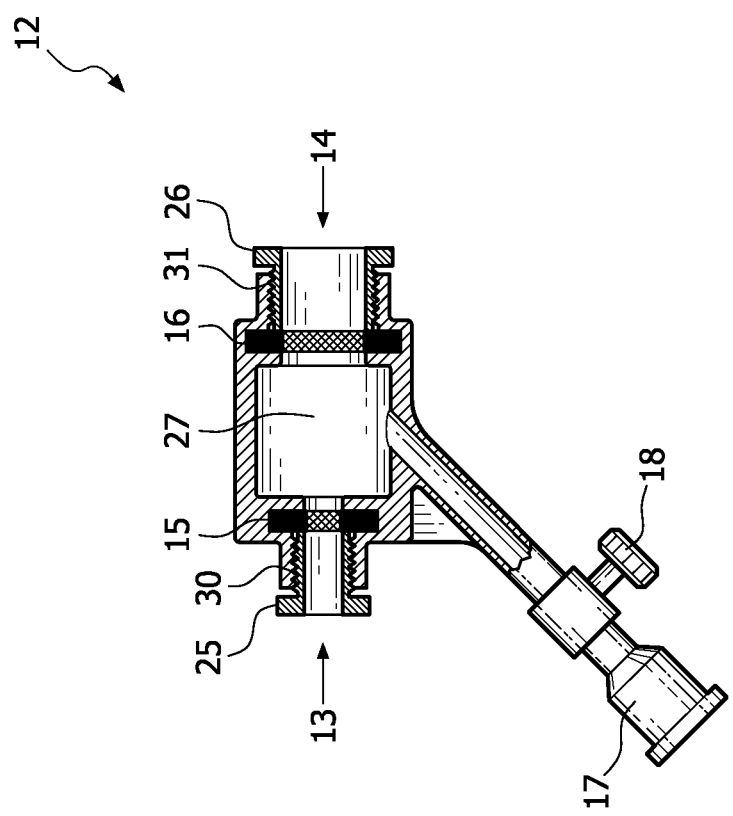

FIG. 9: shows a cross-sectional view of an inflation coupling, wherein the ports are disposed with screw-fit couplings.

Figure 10:
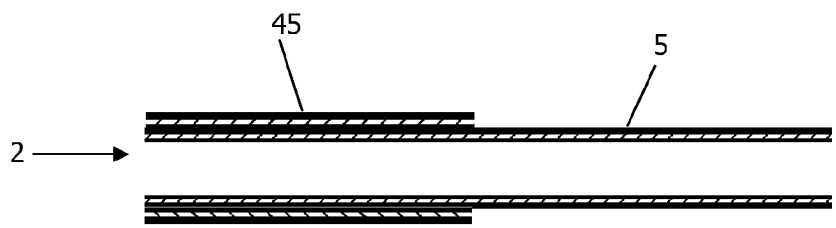

FIG. 10: shows a cross-sectional view of a proximal end of an elongated catheter tube 5, disposed with an outer reinforcing tube.

Figure 11:
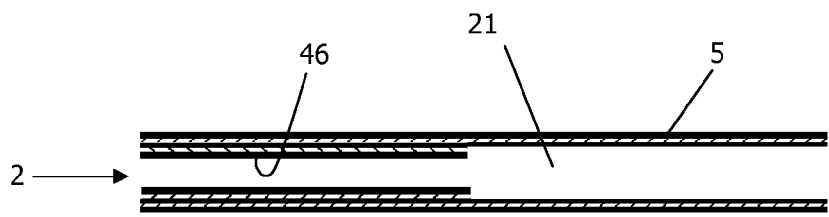

FIG. 11: shows a cross-sectional view of a proximal end of an elongated catheter tube 5, disposed with an inner reinforcing tube.

Figure 12:
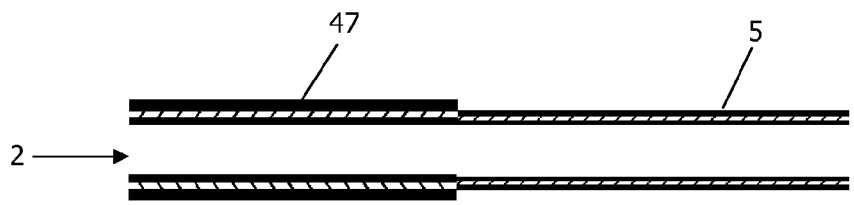

FIG. 12: shows a cross-sectional view of a proximal end of an elongated catheter tube 5, extended with a reinforcing tube.

Figure 13:
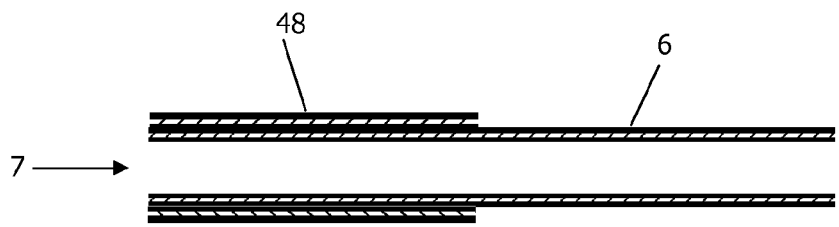

FIG. 13: shows a cross-sectional view of a proximal end of a removable inner tube, disposed with an outer reinforcing tube.

Figure 14:
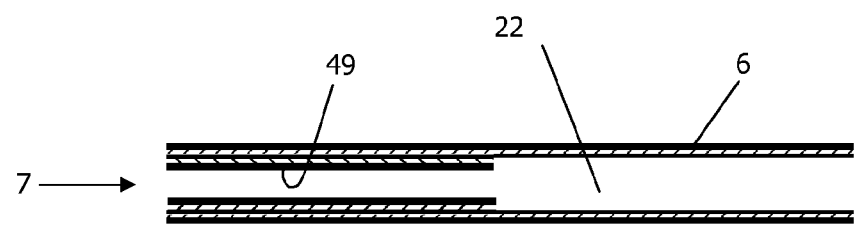

FIG. 14: shows a cross-sectional view of a proximal end of a removable inner tube, disposed with an inner reinforcing tube.

Figure 15:
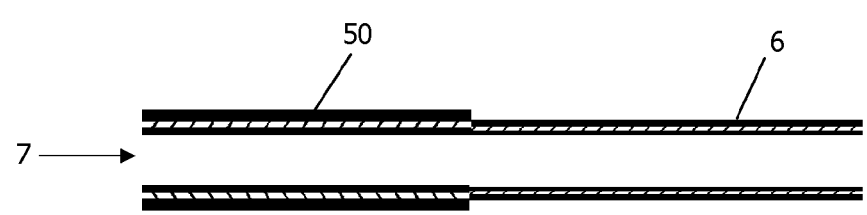

FIG. 15: shows a cross-sectional view of a proximal end of a removable inner tube, extended with a reinforcing tube.

Figure 16:
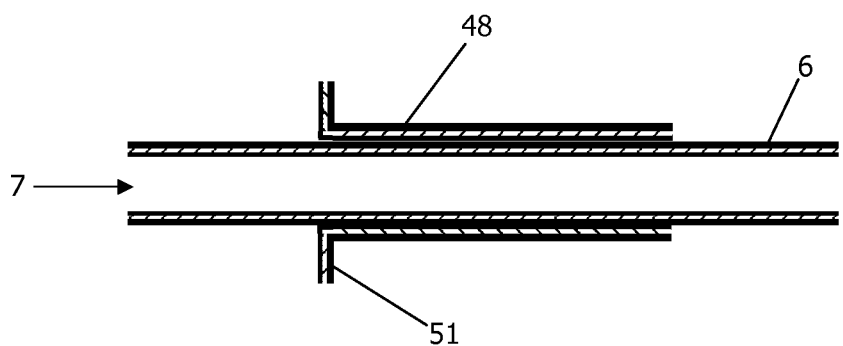

FIG. 16: shows a cross-sectional view of a proximal end of a removable inner tube, disposed with an outer reinforcing tube having an annular ridge.

SUMMARY OF THE INVENTION

One embodiment of the invention is a kit for delivering catheter brachytherapy to a subject comprising:
  a medical balloon catheter (1) having a proximal (2) end and distal (3) end, comprising an elongated catheter tube (5) with an inflation lumen (21) extending therewithin and at least one inflatable balloon (4, 4') towards the distal end (3) in fluid communication with the catheter tube (5) inflation lumen (21), wherein the inflation lumen (21) is configured to carry inflation fluid to the least one inflatable balloon (4, 4') in the presence of the removable inner tube (6);

a removable inner tube (6) having an elongated body, and open (9) proximal (7), a closed (10) distal end (8) and a source wire lumen (22) extending therewithin, said removable inner tube (6) configured for insertion into and removal from at least part of the length of the inflation lumen (21), source wire lumen (22) configured to receive a source wire (19) bearing a therapeutic radiation source (20).

Another embodiment of the invention is a kit for delivering brachytherapy to a subject comprising:

a medical balloon catheter (1) having a proximal (2) and distal (3) end, comprising a elongated catheter tube (5) with an inflation lumen (21) extending therewithin and at least one inflatable balloon (4, 4') towards the distal end (3) in fluid communication with the catheter tube (5) inflation lumen (21), the catheter tube (5) configured to unfold from a kinked condition permitting the inflation lumen (21) to slidably receive a removable inner tube (6), the inflation lumen (21) configured to carry inflation fluid to the least one inflatable balloon (4, 4') in the presence of the removable inner tube (6); and a removable inner tube (6) having an elongated body, an open (9) proximal end (7), a closed (10) distal end (8), and a source wire lumen (22) extending therewithin, wherein the removable inner tube (6) is configured for insertion into and removal from at least part of the length of the inflation lumen (21), and the source wire lumen (22) configured to receive a source wire (19) bearing a therapeutic radiation source (20).

Another embodiment of the invention is a kit for delivering brachytherapy to a subject comprising:

a medical balloon catheter (1) having a proximal (2) and distal (3) end, comprising a elongated catheter tube (5) with an inflation lumen (21) extending therewithin and at least one inflatable balloon (4, 4') towards the distal end (3) in fluid communication with the catheter tube (5) inflation lumen (21), wherein the catheter tube (5) is kinkable and the inflation lumen (21) is configured to: accommodate a removable inner tube (6), and carry inflation fluid to the least one inflatable balloon (4, 4') in the presence of the removable inner tube (6); and a removable inner tube (6) having an elongated body, an open (9) proximal end (7), a closed (10) distal end (8), and a source wire lumen (22) extending therewithin wherein the removable inner tube (6) is non-kinkable, wherein the removable inner tube (6) is configured for insertion into and removal from at least part of the length of the inflation lumen (21), and the source wire lumen (22) configured to receive a source wire (19) bearing a therapeutic radiation source (20).

Another embodiment of the invention is a kit as defined above, further comprising an inflation coupling (12) configured to couple the proximal end of the catheter tube (5) to an inflation pump to allow inflation of the balloon (4) and access to the open (9) proximal end (7) of the removable inner tube (6) when said removable inner tube (6) is inserted into the inflation lumen (21), during inflation.

Another embodiment of the invention is a kit as defined above, wherein said inflation coupling (12) comprises:

a distal port (14), disposed with a distal seal (16),
a proximal port (13) disposed with a proximal seal (15), and
pump coupling (17) operably connected to a valve, which ports (13, 14) and pump coupling (17) are in fluid connection with a chamber (27) in the coupling (12), wherein the distal port (14) is configured to accept the proximal end of the catheter tube (5), and to form a seal against the body of the catheter tube (5), and the proximal port (13) is configured to accept the removable inner tube (6) and to form a seal against the body of the removable inner tube (6) distal to the opening (9), allowing the proximal end of the removable inner tube (6) to pass through the coupling (12).

Another embodiment of the invention is a kit as defined above, wherein an outer diameter of the catheter tube (5) is between 2 mm and 6 mm.

Another embodiment of the invention is a kit as defined above, wherein the catheter tube (5) has a flexural rigidity that is less than that of the removable inner tube (6).

Another embodiment of the invention is a kit as defined above, wherein the catheter tube (5) is made from silicone rubber or from polyurethane.

Another embodiment of the invention is a kit as defined above, wherein the catheter tube (5) is made from polyurethane or a polyurethane-containing compound.

Another embodiment of the invention is a kit as defined above, wherein the diameter of the inflation lumen (21) is between 5% and 20% greater than the outer diameter of the removable inner tube (6).

Another embodiment of the invention is a kit as defined above, wherein the catheter tube (5) is disposed with a non-distensible cord between its proximal (2) and distal ends (3) which prevents longitudinal distension of the medical catheter (1).

Another embodiment of the invention is a kit as defined above, wherein the cord is disposed within, outside or inside the wall of the catheter tube (5).

Another embodiment of the invention is a kit as defined above, wherein the proximal end of the catheter tube (5) is reinforced to reduce deformation by the application of circumferential pressure.

Another embodiment of the invention is a kit as defined above, wherein said reinforcement comprises an outer tube disposed over the proximal end of the catheter tube (5);

an inner tube inserted into the proximal end of the catheter tube (5); or an extension to the proximal end of the catheter tube (5).

Another embodiment of the invention is a kit as defined above, wherein the medical catheter (1) comprises visible graduations marked at least partly along the length catheter tube (5).

Another embodiment of the invention is a kit as defined above, wherein the wall of removable inner tube (6) has a thickness of between 0.1 mm and 0.4 mm.

Another embodiment of the invention is a kit as defined above, wherein the flexural rigidity of the removable inner tube (6) is greater than that of the catheter tube (5).

Another embodiment of the invention is a kit as defined above, wherein the proximal end of the removable inner tube (6) is reinforced to reduce deformation by the application of circumferential pressure.

Another embodiment of the invention is a kit as defined above, wherein said reinforcement comprises a reinforcing outer tube (48) disposed over the removable inner tube (6) at or towards the proximal end;

a reinforcing inner tube (49) inserted into the removable inner tube (6) at or towards the proximal end; or a reinforcing extension (50) to the proximal end of the removable inner tube (6).

Another embodiment of the invention is a kit as defined above, where the reinforcing outer tube (48) disposed over the removable inner tube (6), is disposed with an annular ridge (51) at or towards the proximal end of the reinforcing tube (48).

Another embodiment of the invention is a kit as defined above, wherein the removable inner tube (6) comprises visible graduations marked at least partly along its length.

Another embodiment of the invention is a kit as defined above, wherein a flexural rigidity of removable inner tube (6) is between 1% and 60% greater than that of the catheter tube (5).

Another embodiment of the invention is a kit as defined above, wherein the removable inner tube (6) is made of polypropylene, polytetrafluoroethylene (PTFE), PEEK (polyetheretherketone) or polyethylene.

Another embodiment of the invention is a kit as defined above, wherein the removable inner tube (6) is made of polyimide, PEEK (polyetheretherketone) or polyethylene.

Another embodiment of the invention is a kit as defined above, wherein the diameter of the source wire lumen (22) of the removable inner tube (6) is between 0.5 mm and 1.9 mm.

Another embodiment of the invention is a kit as defined above, wherein the removable inner tube (6) is between 3 and 90 cm longer than the medical balloon catheter (1).

Another embodiment of the invention is a kit as defined above, further comprising a removable pusher wire (11) configured for insertion into and removal from the inflation lumen (21) to provide rigidity to the catheter tube (5) during insertion into a subject via a nasopharyngeal route.

Another embodiment of the invention is a kit as defined above, wherein said pusher wire (11) has a flexural rigidity that is greater than that of the removable inner tube (6).

Another embodiment of the invention is a kit as defined above, further comprising an inflation pump (30).

Another embodiment of the invention is a kit as defined above, where the medical balloon catheter is configured for insertion into the oesophagus via the nasopharyngeal route.

Another embodiment of the invention is a kit as defined above, where the medical balloon catheter is configured for insertion into the uterine cavity via the cervical route.

Another embodiment of the invention is a kit as defined above, where the medical balloon catheter is configured for insertion into breast tissue via an incision or needle puncture in the breast.

Another embodiment of the invention is a method for delivering catheter brachytherapy to a subject comprising:
  inserting a deflated medical balloon catheter (1) into the oesophagus of a subject via the nasopharyngeal route, said medical balloon catheter (1) having a proximal (2) end and distal (3) end, comprising an elongated catheter tube (5) with an inflation lumen (20) extending therewithin and at least one inflatable balloon (4, 4') towards the distal end (3) in fluid communication with the catheter tube (5) inflation lumen (21), wherein the inflation lumen (21) is configured to carry inflation fluid to the least one inflatable balloon (4, 4') in the presence of the removable inner tube (6);
  positioning the at least one inflatable balloon (4, 4') in the region of treatment,
  inserting a removable inner tube (6) into the inflation lumen (21), said removable inner tube (6) having an elongated body, and open (9) proximal (7), a closed (10) distal end (8) and a source wire lumen (22) extending therewithin, wherein,
    said removable inner tube (6) configured for insertion into and removal from at least part of the length of the inflation lumen (21),
    source wire lumen (22) configured to receive a source wire (19) bearing a therapeutic radiation source (20),
  inflating the at least one inflatable balloon (4, 4'),
  advancing a radiation source wire (19) through the source wire lumen (22) to the region of treatment, and administering a radiation dose,
  removing the radiation source wire (19),
  deflating the at least one inflatable balloon (4, 4'),
  withdrawing the removable inner tube (6),
  optionally leaving the medical balloon catheter (1) in situ for a subsequent treatment session.

Another embodiment of the invention is a method for delivering catheter brachytherapy to a subject comprising:
  inserting a medical balloon catheter (1) through an entry point in subject, said medical balloon catheter (1) having a proximal (2) end and distal (3) end, comprising an elongated catheter tube (5) with an inflation lumen (20) extending therewithin and at least one inflatable balloon (4, 4') towards the distal end (3) in fluid communication with the catheter tube (5) inflation lumen (21), the catheter tube (5) configured to unfold from a kinked condition permitting the inflation lumen (21) to slidably receive a removable inner tube (6), the inflation lumen (21) is configured to carry inflation fluid to the least one inflatable balloon (4, 4') in the presence of the removable inner tube (6),
  positioning the at least one inflatable balloon (4, 4') in the region of treatment,
  inserting a removable inner tube (6) into the inflation lumen (21), said removable inner tube (6) having an elongated body, and open (9) proximal (7), a closed (10) distal end (8) and a source wire lumen (22) extending therewithin, wherein,
    said removable inner tube (6) configured for insertion into and removal from at least part of the length of the inflation lumen (21),
    source wire lumen (22) configured to receive a source wire (19) bearing a therapeutic radiation source (20),
  inflating the at least one inflatable balloon (4, 4'),
  advancing a radiation source wire (19) through the source wire lumen (22) to the region of treatment, and administering a radiation dose,
  removing the radiation source wire (19),
  deflating the at least one inflatable balloon (4, 4'),
  withdrawing the removable inner tube (6),
  optionally leaving the medical balloon catheter (1) in situ for a subsequent treatment session.

Another embodiment of the invention is a method for delivering catheter brachytherapy to a subject comprising:
  inserting a medical balloon catheter (1) through an entry point in subject, said medical balloon catheter (1) having a proximal (2) end and distal (3) end, comprising an elongated catheter tube (5) with an inflation lumen (20) extending therewithin and at least one inflatable balloon (4, 4') towards the distal end (3) in fluid communication with the catheter tube (5) inflation lumen (21), wherein the catheter tube (5) is kinkable and the inflation lumen (21) is configured to:
    accommodate a removable inner tube (6),
    carry inflation fluid to the least one inflatable balloon (4, 4') in the presence of the removable inner tube (6),
  positioning the at least one inflatable balloon (4, 4') in the region of treatment, inserting a removable inner tube (6) into the inflation lumen (21), said removable inner tube (6) having an elongated body, and open (9) proximal (7), a closed (10) distal end (8) and a source wire lumen (22) extending therewithin, wherein the removable inner tube (6) is non-kinkable, said removable inner tube (6) configured for insertion into and removal from at least part of the length of the inflation lumen (21), source wire lumen (22) configured to receive a source wire (19) bearing a therapeutic radiation source (20), inflating the at least one inflatable balloon (4, 4'), advancing a radiation source wire (19) through the source wire lumen (22) to the region of treatment, and administering a radiation dose, removing the radiation source wire (19), deflating the at least one inflatable balloon (4, 4'), withdrawing the removable inner tube (6), optionally leaving the medical balloon catheter (1) in situ for a subsequent treatment session.

Another embodiment of the invention is a method as defined above, wherein a pusher wire (11) is inserted into the inflation lumen (21) prior to advancement of the medical balloon catheter (1) through the body to give temporary rigidity to the medical balloon catheter (1).

Another embodiment of the invention is a method as defined above, wherein an inflation coupling (12) as defined above is coupled to the catheter tubing (5) at the proximal end (2) of the medical balloon catheter (1), after insertion of the catheter (1) into the oesophagus of a subject via the nasopharyngeal route and prior to inserting the removable inner tube (6) into the inflation lumen (21).

Another embodiment of the invention is a method as defined above, wherein the inflation coupling (12) is further coupled to the proximal end (7) of the removable inner tube (6) after inserting the removable inner tube (6) into the inflation lumen (21).

Another embodiment of the invention is a method as defined above, wherein the inflation coupling (12) is removed from the medical balloon catheter (1) after withdrawing the removable inner tube (6).

Another embodiment of the invention is a method as defined above, wherein a proximal part of medical balloon catheter (1) is fixed with an adhesive plaster to the body the patient after insertion into the body and/or between treatment sessions.

Another embodiment of the invention is a method as defined above, wherein the treatment is fractionated.

Another embodiment of the invention is a method as defined above, wherein the medical balloon catheter (1) is left in situ for between 3 to 21 days.

Another embodiment of the invention is a method as defined above, wherein the medical balloon catheter (1) is inserted into the oesophagus of the subject via the nasopharyngeal route, for the delivery of brachytherapy to the oesophagus.

Another embodiment of the invention is a method as defined above, wherein a proximal part of medical balloon catheter (1) is fixed with a plaster to the nose of the patient after insertion via the nasopharyngeal route and/or between treatment sessions.

Another embodiment of the invention is a method as defined above, wherein the medical balloon catheter (1) is inserted into the uterine cavity of the subject via the cervical route for the delivery of brachytherapy to the uterine cavity.

Another embodiment of the invention is a method as defined above, wherein a proximal part of medical balloon catheter (1) is fixed with a suture to the exit of the cervix after insertion via the cervical route and/or between treatment sessions.

Another embodiment of the invention is a method as defined above, wherein the medical balloon catheter (1) is inserted into the breast tissue of the subject via an incision in the breast for the delivery of brachytherapy to the breast.

Another embodiment of the invention is a method as defined above, wherein a proximal part of medical balloon catheter (1) is fixed with a plaster where it exits breast after insertion via the incision and/or between treatment sessions.

Another embodiment of the invention is a method as defined above, using a kit as defined above.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The articles "a" and "an" are used herein to refer to one or to more than one, i.e. to at least one of the grammatical object of the article. By way of example, "a lumen" means one lumen or more than one lumen.

The recitation of numerical ranges by endpoints includes all integer numbers and, where appropriate, fractions subsumed within that range (e.g. 1 to 5 can include 1, 2, 3, 4 when referring to, for example, a number of lumens, and can also include 1.5, 2, 2.75 and 3.80, when referring to, for example, measurements). The recitation of end points also includes the end point values themselves (e.g. from 1.0 to 5.0 includes both 1.0 and 5.0)

The present invention relates to a kit and method for delivering catheter brachytherapy to a subject, particularly for fractionated (multiple dose) treatment. It is suitable for treating internal cancers susceptible to catheter brachytherapy, but in particular esophageal, uterine or breast cancers. It is especially suitable for intracavitary, or interstitial brachytherapy. The invention is based on introducing a highly flexible tube through an entry point for treatment such as the nose (for esophageal cancer), vagina (for uterine cancer) or skin puncture or incision (breast cancer), temporarily strengthening and stiffening the tube for the duration of radiation treatment, and subsequently returning the tube to its normal flexibility allowing comfortable wearing between radiotherapy sessions. The flexibility of the tube is such that it can be kinked without damage (i.e. kinkable) or it exhibits low pushability, so offers no or little resistance to bending, so the tube may be comfortably worn, for example, taped to the skin after and between treatments. The flexible tube is also disposed with an inflatable balloon allowing the tube to occupy an internal space, such as the oesophagus, or the uterus, or to create space such as within the breast tissue. Importantly, the present invention allows strengthening and stiffening of the flexible tube by temporarily introducing a more rigid inner tube into a lumen of the flexible tube, which inner tube contains a separate lumen for insertion of the radioactive source wire. The arrangement provides a dry source wire lumen for effective administration of radiotherapy, maintains an even dose of radiation to the treatment region, and provides a high degree of patient comfort.

Referring to FIGS. 1 and 2, one embodiment of the present invention is a kit for delivering catheter brachytherapy to a subject comprising:

a medical balloon catheter 1 having a proximal 2 end and distal 3 end, comprising an elongated catheter tube 5 with an inflation lumen 21 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

a removable inner tube 6 having an elongated body, and open 9 proximal 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20.

Another embodiment of the present invention is a method for delivering brachytherapy to the oesophagus comprising:

inserting a deflated medical balloon catheter 1 into the oesophagus of a subject via the nasopharyngeal route, said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal end 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The kit and method as described herein allow brachytherapy of the esophagus to proceed via the nasopharyngeal route. The medical balloon catheter has a flexible body as described below and can be inserted into the oesophagus via the nasopharyngeal route by a non-specialist. It is known in the art that the insertion of a feeding tube, typically when a subject is nourished after oral surgery, is a technique a nurse can perform without any additional training. The catheter of the invention using the same route and being of similar flexibility may, therefore, be inserted by a non-specialist such as a nurse using the same technique. This is an improvement over the prior art where kits and methods must be utilised by a trained gastroenterologist and which requires the use of an endoscope and guidewire to insert a bulky applicator. By allowing a non-specialist to perform a substantial part of the treatment, the invention saves time of the gastroenterologist and costs of the procedure. This benefit is coupled with the improved patient experience; the procedure can be endured without sedation, and the catheter worn discretely for prolonged periods without discomfort.

Another embodiment of the present invention is a method for delivering brachytherapy to the internal walls of the uterus comprising:

inserting a deflated medical balloon catheter 1 into the uterus of a subject via the cervical route, said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the catheter tube 5 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal end 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The medical balloon catheter has a flexible body as described below and can be inserted into the uterus via the cervix uter by a non-specialist. It is known in the art that the insertion of a hysterometer inside the uterine cavity, is a technique a radiation oncologist can perform without any additional training. The catheter of the invention using the same route and being of similar flexibility may, therefore, be inserted by a non-specialist such as a radiation oncologist using the same technique. This is an improvement over the prior art where kits and methods must be utilised by a trained gynecologist and which requires the insertion of a bulky applicator. By allowing a non-specialist to perform a substantial part of the treatment, the invention saves time of the gynecologist and costs of the procedure. This benefit is coupled with the improved patient experience; the procedure allows fractionated treatment, and the catheter worn discretely for prolonged periods without discomfort.

Another embodiment of the present invention is a method for delivering brachytherapy to a breast resection cavity comprising:

inserting a deflated medical balloon catheter 1 into a breast resection cavity of a subject after a breast tumour has been removed (e.g. breast conserving surgery), said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal end 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The medical balloon catheter can be inserted into the breast resection cavity via the surgical scar or through the skin. The catheter worn discretely for prolonged periods without discomfort.

The ease with which the device can be worn, inserted and withdrawn allows prolonged fractionated curative treatments. The daily radioactive dose can be lowered, and delivered in a plurality of sessions for example between 10 and 30 treatments, with substantial intervals between the treatments (e.g. daily). Fractionated treatment with a lower radiation dose reduces damage to the tissue thereby lowering the possibility of scarring (fibrosis and subsequent stenosis). In the case of oesophageal cancer, it can prevent closure of the oesophageal tube due to late occurring fibrosis. By contrast, conventional treatment must deliver a high dose at each session because the patient cannot withstand more than a few (e.g. 3 to 5) treatments, owing to the stress and discomfort of inserting and wearing the applicator. As a consequence, stenosis of the oesophageal tube (due to fibrosis) is common in the prior art.

Fractionated (multiple, e.g. 5 to 30) treatments are better tolerated by the tissues compared with delivering high doses in one to three treatments. For instance a boost after external radiotherapy (50 Gy) may be given with 3 times 5 Gy twice a week, total dose 15 Gy, or by giving 20 Gy in 10 sessions. If the patient is not operated, there is a higher risk of fibrosis and stenosis by giving 3 times 5 Gy instead of 10 times 2 Gy. This means the patient will have to undergo later on dilatations regularly, for example, to open the esophageal lumen. This is traumatic and painful.

The Gérard-Bonvoisin probe (by Nucletron, Veenendael, The Netherlands) of the prior art for oesophageal brachytherapy may allow one to three sessions of treatment but which will be felt as very aggressive and traumatic by the semi-conscious patients even under conventional light anesthesia. The much less traumatic system of the present invention allow ambulatory fractionated treatments that improve the dose escalation possibilities and improve the cure rate for patients suffering from esophageal cancer. For example, delivering 20 Gy using fractionated brachytherapy becomes feasible, and greatly improves the approach of oesophageal cancer treatment.

For patients who will be operated, the addition of brachytherapy to chemotherapy and external radiotherapy increases the total eradication of living cancer cells on pathological samples. As it is shown in many clinical trials dealing with esophageal cancer, that only complete responders to radio-chemotherapy survive in the long term, there is a need to raise the percentage of complete responders from 30-50% today to 50-70%, possibly using the present invention, in order to increase the cure rates of oesophageal cancer treatments.

For palliative treatments, user-friendly fractionated brachytherapy becomes an additional tool, in combination with intra-oesophageal stents for instance, in order to increase the progression-free interval in this very aggressive disease.

The terms "distal" and "proximal" are used through the specification, and are terms generally understood in the field to mean towards (proximal) or away (distal) from the surgeon side of the apparatus. Thus, "proximal" means towards the surgeon side and, therefore, away from the patient side. Conversely, "distal" means towards the patient side and, therefore, away from the surgeon side.

The medical balloon catheter 1 (FIG. 1) having a proximal 2 end and distal 3 end, comprises an elongated catheter tube 5 with an inflation lumen 21 extending therewithin and at least one inflatable balloon 4, 4' towards the distal end 3 in fluid communication with the catheter tube 5 inflation lumen 21. The distal end of the medical catheter 1 is sealed.

The medical balloon catheter 1 may be extended at the distal end 3 by a flexible tail formed from elongated catheter tube 5 which extended tail can act as a stabilising longitudinal anchor when the device is used for treating esophageal cancer. The tail anchor against the esophageal wall, reducing the possibility that the medical catheter 1 is expelled by the subject by coughing or sneezing.

The size of the medical balloon catheter 1 is sufficiently narrow to introduce through the appropriate passage way e.g. nasopharyngeal route, vaginal and cervical route, or through a skin puncture. It is flexible enough not to damage when kinked and does not have the requisite pushability per se for advancement to the site of treatment. These are determined by the properties of the elongated catheter tube 5 and balloon 4, 4' discussed below in detail.

The design of the medical balloon catheter 1 advantageously facilitates insertion with the assistance of a pusher wire, withdrawal and wearing. In wearing, the proximal end of the catheter tube 5 may be fixed to the skin, for example, in the case of esophageal treatment, fixed on the nostril and kinked around the nostril and/or the cheek using adhesive strips, particularly hypoallergenic adhesive strips. Fixation to the nostril provides a stable and accurate positioning of the treating portion of medical catheter 1 which corresponds to the balloon area. This fixed part, kinked through wearing, may be regularly unfolded or 'unkinked', prior to each treatment session, in order to proceed with the insertion of the removal inner tube 6 allowing source introduction. Fixation to the skin can be applied similarly to the treatment of other cancers, at the point where the catheter exits the body.

The medical balloon catheter 1 comprises an elongated catheter tube 5 (FIG. 1) provided with an open proximal end 2 providing access to the inflation lumen 21 which extends the longitudinal length of the tube. The proximal end provides an opening through which inflation fluid can enter, for the insertion of the inner removable inner tube 6, and for insertion of a pusher wire 11.

In fluid connection with the inflation lumen 21 is at least one inflatable balloon located towards the distal end 3 of the catheter tube 5. The inflation lumen 20 may be in fluid connection with the at least one inflatable balloon 4, 4' via a plurality of apertures 30 in wall of the catheter tube 5. An application of inflation fluid such as saline through the inflation lumen 21 causes the at least one inflatable balloon 4, 4' to open, expanding in a radial direction allowing contact with the wall of the oesophagus.

The elongated catheter tube 5 may terminate immediately distal to the distal balloon(s) or may extend further in the direction distal to the balloon(s) so giving the medical balloon catheter 1 an extended tail that can act as a stabilising longitudinal anchor against the esophageal wall. The tail reduces the possibility that the medical catheter 1 is expelled by the subject by coughing or sneezing. The distal end of the elongated catheter tube 5 is sealed.

The diameter of elongated catheter tube 5 is sufficiently narrow to introduce through the appropriate passage way e.g. nasopharyngeal route, vaginal and cervical route, or through a skin puncture. The elongated catheter tube 5 can be described as being flaccid or kinkable. It has insufficient pushability, that is the ability to transfer forces from the proximal to the distal end of the catheter, for advancement through the entry point to the site of treatment, for instance, through the appropriate passage way e.g. nasopharyngeal route, vaginal and cervical route, or through a skin puncture. Being kinkable or flaccid means it can be folded, e.g. at least in half to a degree to induce a collapse in the tube-shaped wall, giving rise to a fold line that is known as a kink or crease. The kink crosses the longitudinal axis of the elongated catheter tube 5. Because the elongated catheter tube 5 has a kinkable quality, unfolding the tube will remove the kink, without damage to the wall of the elongated catheter tube 5. More importantly, the integrity and dimensions of the tube elongated catheter tube 5, particularly of the inflation lumen 21 are not affected, so that insertion of the removable inner tube is not hindered kink-damaged walls. Thus, the elongated catheter tube 5 may be folded without damage to the wall of the elongated catheter tube 5 such that the inflation lumen 21 in the unfolded or unkinked condition, can slidably receive the removable inner tube 6; the removable inner tube 6 is able to advance past the position of the kink without substantial hindrance. The elongated catheter tube 5 is flaccid enough not to damage when kinked. This is a departure from usual catheter tubing made from a non-kinkable material, normally providing enough flexibility for steering through a tortuous path and sufficient stiffness to give good pushability, that is the ability to transfer forces from the proximal to the distal end of the catheter. However, such tubing of the art but cannot endure kinking without damage to the wall of the tube. Furthermore, such catheters of the art are too stiff to be comfortable for prolonged wearing. The terms "kinkable" and "non-kinkable" are known in the field.

According to one embodiment of the invention, the flexibility of a tube is described in terms of properties that are relatively easy to measure, for example, the diameter of a tube cross section and the elastic (Young's) modulus E of the material or materials. If a tube is composed of a single material, flexibility can be defined as the inverse of the product of the moment of inertia I of the cross-section with respect to the bending axis and the Young's modulus E. The product EI is known in scientific literature as the "flexural rigidity" of the beam. For a round wire with single material the moment of inertia I is $\pi d^4/64$, where d is the external diameter of the tube. Accordingly, the flexural rigidity is then $EI=\pi d^4/64$. This defines flexibility of a tube at a point. Thus, if EI is doubled the tube is said to be twice as stiff.

By holding one end of the tube fixed, applying a known weight or force perpendicular to the tube axis at the other end of the uniform section, the deflection from the original straight axis will be proportional to the flexibility, i.e., inversely proportional to the flexural rigidity of the tube. The deflection will also be proportional to the force or weight applied, as well as the cube of the length tested. Thus, the deflection corresponding to a known load or the force required to cause a known deflection, can be used as a direct measure of the tube's flexibility or flexural rigidity. A test for deflection is described, for example, in EP 1 666 083 which is incorporated herein by reference.

According to one aspect of the invention, the flexural rigidity in grams of the catheter tube 5 is less than that of the removable inner tube 6. The flexural rigidity of the catheter tube 5 may be equal to or greater than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70% or 80% less than that of the removable inner tube 6, or a value between any two of the aforementioned values. Preferably, the flexural rigidity in grams of the catheter tube 5 is between 1 and 60% less than that of the removable inner tube 6.

As mentioned above, the catheter tube 5 may not have the requisite pushability for advancement through the entry point of the subject and to the site of treatment. According to one aspect of the invention, the pushability of the catheter tube 5 is less than that of the removable inner tube 6. The removable inner tube 6 is more typical of catheter tubing of the art in that it provides sufficient pushability, in this instance for advancement through the inflation lumen 21 of the catheter tube 5.

According to another aspect of the invention, the catheter tube 5 has a shape recovery property that enables it to deform upon the application of a mechanical force (e.g. tensile, compression), and to restore its previous shape when the force is removed. The property permits the catheter tube 5 to bend and kink without damage, more in particular to maintain the integrity of the lumen 21 allowing passage of the removable inner tube 6 therethrough substantially unhindered. In tubing showing a lower shape recovery property, such as the removable inner tube 6, bending that leads to a fold line kink that permanently damages the source wire lumen 22 and prevents or hinders free passage of the source wire 19.

The catheter tube 5 is made from any suitable material which provides the requisite properties (e.g. a non-kinkable, low/insufficient pushability etc.) with sufficient strength to withstand inflation pressure and is biocompatible. Suitable materials are known in the art and not limited, such as polyurethane or polyurethane-containing compounds.

The diameter of the inflation lumen 21 of the catheter tube 5 is configured to accommodate a removable inner tube 6. The diameter of the inflation lumen 21 of the catheter tube 5 should be sufficiently larger than the outer diameter of the removable inner tube 6 to allow the removable inner tube 6 to be easily advanced and removed from the inflation lumen 21. Generally diameter of inflation lumen 21 will be 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% greater than the outer diameter of the removable inner tube 6.

According to one aspect of the invention, the diameter of the inflation lumen 21 is 1.2, 1.3, 1.4 mm, 1.5 mm, 1.6 mm, 1.7 mm, 1.8 mm, 1.9 mm, 2.0 mm 2.2 mm, 2.4 mm, 2.6 mm, 2.8 mm, 3.0 mm, 3.2 mm, 3.4 mm, 3.6 mm, 3.8 mm, 4.0 mm or a value between any two of the aforementioned values, preferably between 1.4 mm and 2.8 mm.

According to one aspect of the invention, the wall of the catheter tube 5 has a thickness of 0.1 mm, 0.2 mm, 0.3 mm, 0.4 mm, 0.5 mm, 0.6 mm, 0.7 mm, 0.8 mm, 0.9 mm, 1.0 mm or a value between any two of the aforementioned values, preferably between 0.1 mm and 0.4 mm.

According to one aspect of the invention, the external diameter of the catheter tube 5 is 2 mm, 3 mm, 4 mm, 5 mm, 6 mm or a value between any two of the aforementioned values, preferably between 3 mm and 4 mm.

According to one aspect of the invention, the catheter tube 5 is formed from a single piece of tubing from the proximal end 2 to the first proximal balloon 4. According to one aspect of the invention, the catheter tube 5 is formed from a single piece of tubing from the proximal end 2 to the last, distal balloon 4'.

According to one aspect of the invention, the catheter tube 5 is reinforced at the proximal 2 end to prevent or reduce deformation by the application of circumferential pressure; such circumferential pressure may be applied by an inflation coupling described below. It may be reinforced by increasing the thickness of the wall at the proximal end, for example, by the use of an outer nitenol or polyetheretherketone (PEEK) tube. This embodiment is depicted in FIG. 10 whereby a tube 45 of nitenol or PEEK is attached to the outside of the catheter tube 5 in a coaxial arrangement. Alternatively, it may be reinforced by increasing the thickness of the wall at the proximal end, for example, by the use of an inner nitenol or PEEK tube. This embodiment is depicted in FIG. 11 whereby a tube 45 of nitenol or PEEK is inserted into the inflation cavity 21 of the catheter tube 5 in a coaxial arrangement. Alternatively, it may be reinforced by an extension tubing, which joins to the proximal end of the catheter tube by bonding or welding, which extension tubing is made from tubing with the requisite circumferential compression strength such as braided tubing, nitenol or PEEK tubing. This embodiment in depicted in FIG. 12 whereby a tube 47 of nitenol or PEEK is attached to the proximal end the catheter tube 5. Such extension pieces are commonly employed in the art, and it is well within the practices of the skilled person to adapt the invention to include such extension pieces. The reinforcement facilitates attachment to an inflation coupling which seals using circumferential pressure applied to the wall of the catheter tube 5 by preventing distortion of the catheter tube 5. The length of the reinforced part 45, 46, 47 may be between 0.5 cm and 5 cm.

According to one aspect of the invention, a non-distensible cord is disposed between the proximal and distal end of the medical catheter 1 or catheter tube 5 or which cord prevents longitudinal distension of the medical catheter 1 or catheter tube 5, particularly when introducing or removing the removable inner tube 6. The cord may be provided within, outside or inside the wall of the catheter tube 5, being attached at least at the proximal 2 and distal ends 3 of the medical catheter 1. The cord provides constant length to the medical catheter 1 when introducing the removable inner tube 6 that allows source introduction. Preferably the cord is made from stainless steel, titanium, platinum, nickel, polytetrafluoroethylene (PTFE), PEEK or other suitable biocompatible material.

According to one aspect of the invention, the medical catheter 1 comprises visible graduations marked at least partly along the length catheter tube 5 wall. The graduations may allow the user to identify the length of medical catheter—relative to the nostril edge for instance—1 required for insertion such that the balloons 4, 4' or other distal part align with the region to be treated. They also permit subsequent medical catheters 1 to be inserted and duly aligned, for example, during fractionated treatment by inserting to a depth previously determined, thereby obviating the requirement for a body scanner during subsequent insertions. According to one aspect of the invention, the graduations are present in the proximal 2 half of the medical catheter 1. According to another aspect of the invention, the graduations are marked in centimeters with regular numeric indications.

It should be appreciated that although the catheter 1 and removable inner tube 6 utilizes a co-axial assembly, it is possible to utilize a multilumen design which provides a separate inflation lumen for inflating the balloon(s) and one or more separate lumens which functions to hold the removable inner tube 6, pusher wire 11 and source wire 19.

The design of the catheter tube 5 advantageously facilitates insertion, withdrawal and wearing. In wearing, the proximal end of the catheter tube 5 may be fixed on the nostril and kinked around the nostril and/or the cheek using adhesive strips, particularly hypoallergenic adhesive strips. Fixing provides a stable positioning of the treating portion of medical catheter 1 which corresponds to the balloon area. This fixed part may be regularly 'unkinked', prior to each treatment session, in order to proceed with the insertion of the removal inner tube 6 allowing source introduction.

The medical catheter 1 is provided with one of more balloons (e.g. 2, 3, 4, 5, 6, 7, 8) 4, 4' in fluid communication with the inflation lumen 21 of the elongated catheter tube 5. The one or more balloons 4, 4' (referred to "the balloon" herein, unless otherwise indicated) is an inflatable member that expands radially to contact the wall of vessel or tissue being treated. Such balloons are well known in the art. In the case of esophageal cancer, the function of the balloon is to fill the esophageal lumen and bring the medical catheter 1 in alignment with the central axis of the esophagus in the region of the balloon, so the dosage of radiation is provided evenly to the walls of the esophagus. In the case of uterine cancer, the function of the balloon is to fill the uterine cavity and bring the medical catheter 1 in alignment with the centre of the cavity in the region of the balloon, so the dosage of radiation is provided evenly to the walls of the uterus. In the case of breast cancer, the function of the balloon is to fill the tumor resection cavity in the breast tissue and bring the medical catheter 1 in alignment with the centre of the created cavity in the region of the balloon, so the dosage of radiation is provided evenly to the surrounding walls of the breast tissue. In use, the balloon is held in its expanded condition (FIG. 7, 8) for a time sufficient to allow the radiation dose to affect those cells which would otherwise continue to proliferate. Preferably, a sufficient dose of radiation can be delivered from about one minute to about sixty minutes to treat the cancer. In its expanded condition, the balloon presses against or at least comes into close proximity with the walls of the esophagus and in doing so centers the radiation source. Centering of this radiation source is important so that all portions of the tissue or vessel receive as close to uniform and equal amounts of radiation as possible. Also centering helps prevents radiation burns or hot spots from developing on portions of the target area.

The balloon 4, 4' in the uninflated state may be provided as a plurality of radially and axially extending "wings" spaced from one another in the circumferential direction around the central longitudinal axis of the balloon. The wings may be wrapped or folded laterally in the manner desired. An elastic sleeve may be disposed around the folded balloon. The balloon 4, 4' is configured to inflate essentially radially, to an extent that the inner walls of the esophagus are contacted. The balloon 4, 4' may be configured to refold with a relatively compact cross section after it has been inflated and deflated. This feature facilitates withdrawal of the deflated catheter from the patient.

According to one aspect of the invention, the external diameter of the balloon 4, 4' in the uninflated state is 3 mm, 4 mm, 5 mm, 6 mm or a value between any two of the aforementioned values, preferably between 3 mm and 4 mm.

According to one aspect of the invention, the external diameter of the balloon 4, 4' in the inflated state is 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm or a value between any two of the aforementioned values, preferably between 10 mm and 50 mm. For the treatment of esophageal cancer, the external diameter of the balloon 4, 4' in the inflated state is preferably between 10 mm and 35 mm. For the treatment of uterine cancer, the external diameter of the balloon 4, 4' in the inflated state is preferably between 15 mm and 35 mm. For the treatment of breast cancer, the external diameter of the balloon 4, 4' in the inflated state is preferably between 30 mm and 50 mm.

The balloon 4, 4' is made from an elastic material such as polyurethane, silicone, latex, poly(ethylene terephthalate) (PET) or polyamide. Conventional balloon materials used in dilatation catheters would be suitable for use with the catheter. Variations can be made in the composition of the materials to vary properties.

The balloon 4, 4' may be attached to the elongated catheter tube 5 using any known technique of the art. For example, techniques commonly used are those which use a short piece of tubing to bind the balloon over the elongated catheter tube 5. One instance is a heat shrinking tubing which binds the balloon over the elongated catheter tube 5. Another is melting the tubing over the elongated catheter tube 5 or gluing the tubing over the elongated catheter tube 5 or welding the tubing over the elongated catheter tube 5. The elongated catheter tube 5 is commonly prepared to receive either technique of attaching a tubing by roughening or modifying the elongated catheter tube 5 bonding surface with either sandblasting or laser carvings.

Radio-opaque markers may be provided on the balloon 4, 4'. They may be provided at predetermined locations near the balloon (e.g. adjacent each axial end of a balloon) to facilitate positioning the balloons at the desired location in the body.

The removable inner tube 6 (FIG. 2) provides a dry lumen for accommodating and guiding the source wire to the point of treatment within the catheter 1. The removable inner tube 6 is an elongated tube, comprising a source wire lumen 22 extended within the removable inner tube 6, which lumen is sealed 10 at a distal end 8. The distal end 8 of the removable inner tube 6 has a non-traumatic tip, for example, rounded. The removable inner tube 6 is open 9 at the proximal end 7, providing access to the lumen 22 by the source wire 19. Importantly, the source wire lumen 22 will remain dry during inflation of the balloon with an inflation fluid, owing to the seal 10 at the distal end 8.

The removable inner tube 6 is sufficiently narrow in external diameter to be introduced into the inflation lumen 21, flexible enough to be steered around the tortuous path of the nasopharyngeal route within the constraints of the inflation lumen 21 and sufficiently rigid to provide pushability. The removable inner tube 6 may be described as being non-kinkable or non-flaccid. Being non-kinkable or non-flaccid means the removable inner tube 6 cannot be kinked without damage to the wall of the tube 6. As explained above, a kink is formed when a tube is folded to induce a collapse in the tube-shaped wall, giving rise to a fold line that is known as a kink. The damage caused by kinking results in one or one or more stress marks. Further, the source wire lumen 22 will become restricted after kinking, thereby preventing proper insertion of the source wire 19. Afterloading machines which advance the source wire 19 through the source wire lumen 22 are sensitive to resistance inside a catheter. If the afterloading machine detects a resistance after a tube has been kinked, the source will be blocked and be automatically withdrawn. Kinking the removable inner tube 6 is to be avoided, therefore. While non-kinkable quality of the removable inner tube 6 provides a certain stiffness and pushability, it also gives enough strength so that the removable inner tube 6 is not deformed by advancement of the source wire 19; a deformable characteristic, as seen, for example in a kinkable or flaccid tube, would be inappropriate for a removable inner tube because insertion of the source may cause a change in the position of the tube; the source position should always be well determined to achieve the correct dosimetry of the treatment. The removable inner tube 6 is made from the material typically used in catheter tubing which provides said properties. As mentioned above, the terms "kinkable" and "non-kinkable" are well known in the field.

According to one aspect of the invention, the flexural rigidity in grams of the removable inner tube 6 is greater than that of the catheter tube 5. The flexural rigidity of the removable inner tube 6 may be equal to or more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 60%, 70% or 80% greater than that of the catheter tube 5, or a value between any two of the aforementioned values. Preferably, the flexural rigidity in grams of the removable inner tube 6 is between 1 and 60% greater than that of the catheter tube 5.

As mentioned above, the removable inner tube 6 has the requisite pushability for advancement through the entry point of the subject and to the site of treatment. According to one aspect of the invention, the pushability of the removable inner tube 6 is greater than that of the catheter tube 5. Pushability refers to the ability to transfer forces from the proximal to the distal end of a tube. More particularly, it is the response of a tube when a longitudinal force is applied along its axis. For small deflections, the tubing properties might be considered to approximate a spring system, in which the longitudinal stiffness of the spring is determined by equation (1), viz $$k_{long} = \frac{EA}{L} \qquad (1)$$

where $k_{long}$ is the longitudinal spring constant, E is the modulus of elasticity, A is the cross-sectional area, and L is the length of the tube. In order to maximize pushability, the skilled artisan would maximise the value of $k_{long}$. In maximizing the pushability of a tube, it would be appreciated that the cross-sectional area of the tube is maximised, the modulus of elasticity is maximised by using a stiff material which still provides the requisite flexibility, and the overall length of the tube is decreased. In the case of the removal inner tube 6 that requires good pushability properties, kinking irreversibly damages the tube wall, and thus a reduced propensity for kinking is an important characteristic. In the case of the elongate tube 5, where a high degree pushability is not desirable, an increased propensity for kinking is acceptable.

According to another aspect of the invention, the removable inner tube 6 has little or no shape recovery property (partially because of its very small wall thickness) such that, after deformation upon the application of a mechanical force (e.g. tensile, compression force), it does not restore its previous shape when the force is removed. This is different from the catheter tube 5 that has a shape recovery property that allows it to bend and kink without damage, more in particular to maintain the integrity lumen 21 allowing passage of the removable inner tube 6 therethrough. By having a lower shape recovery property, bending the removable inner tube 6 to create a fold line kink damages permanently the source wire lumen 22 and prevents or hinders free passage of the source wire 19.

The removable inner tube 6 is made from any suitable material which provides the desired properties (a non-kinkable tube, good pushability) with sufficient stiffness and strength and is biocompatible. Suitable materials are known in the art such as polyimide, PEEK, or polyethylene. The removable inner tube 6 may be coated with a layer of PTFE or Teflon to provide lubricity. Alternatively, the tip of the removable inner tube 6 may be coated with oil. Lubricity aids in the insertion into and withdrawal from the inflation lumen 21, for the whole length of the catheter, which may be up to 1 m in length.

The proximal end of the removable inner tube 6 may be connected to an adapter which can be coupled to a fitting on a radiation afterloading machine, which dispenses the radioactive source wire 19.

The diameter of the source wire lumen 22 of the removable inner tube 6 should be sufficiently larger than the diameter of the radiation source wire 19 to allow the radiation source wire 19 to be easily advanced and removed from the source wire lumen 22. Generally the diameter of the source wire lumen 22 will be 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% greater than the diameter of the radiation source wire 19.

According to one aspect of the invention, the diameter of the source wire lumen 22 is 0.4 mm, 0.5 mm, 0.6 mm, 0.7 mm, 0.8 mm, 0.9 mm, 1.0 mm, 1.2 mm, 1.4 mm, 1.6 mm, 1.8 mm, 1.9 mm or 2.0 mm or a value between any two of the aforementioned values, preferably between 0.5 mm and 1.9 mm, more preferably between 0.5 mm and 1.2 mm.

According to one aspect of the invention, the wall of removable inner tube 6 has a thickness of 0.1 mm, 0.2 mm, 0.3 mm, 0.4 mm, 0.5 mm, 0.6 mm, 0.7 mm, 0.8 mm, 0.9 mm, 1.0 mm or a value between any two of the aforementioned values, preferably between 0.1 mm and 0.4 mm.

According to one aspect of the invention, the removable inner tube 6 comprises graduations marked at least partly along the length removable inner tube 6 wall. The graduations may allow the user to identify the length of removable inner tube 6 required for insertion such that the distal end 8 aligns with the region to be treated. They also permit subsequent removable inner tubes 6 to be inserted and duly aligned, for example, during fractionated treatment by inserting to a depth previously determined, thereby obviating the requirement for a body scanner during subsequent insertions. According to one aspect of the invention, the graduations are present in the proximal 7 half of the removable inner tube 6. According to another aspect of the invention, the graduations are marked in centimeters with regular numeric indications.

According to one aspect of the invention, the removable inner tube 6 is reinforced at or towards the proximal 7 end to prevent or reduce deformation by the application of circumferential pressure; such circumferential pressure may be applied by an inflation coupling described below. It may be reinforced by increasing the thickness of the wall at or towards the proximal end, for example, by the use of an outer nitenol or PEEK tube. This embodiment in depicted in FIG. 13 whereby a tube 48 of nitenol or PEEK is attached to the outside of the removable inner tube 6 in a coaxial arrangement. Alternatively, it may be reinforced by increasing the thickness of the wall at or towards the proximal end, for example, by the use of an inner nitenol or PEEK tube. This embodiment in depicted in FIG. 14 whereby a reinforcing tube 49 of nitenol or PEEK is inserted into the source wire lumen 22 of the removable inner tube 6 in a coaxial arrangement. Alternatively, it may be reinforced by an extension tubing, which joins to the proximal end of the removable inner tube 6 by bonding or welding, which extension tubing is made from tubing with the requisite compression strength such as braided tubing, nitenol or PEEK tubing. Such extension pieces are commonly employed in the art, and it is well within the practices of the skilled person to adapt the invention to include such extension pieces. This embodiment in depicted in FIG. 15 whereby a reinforcing tube 50 of nitenol or PEEK is attached to the proximal end removable inner tube 6. The reinforcement facilitates attachment to an inflation coupling which seals using circumferential pressure applied to the wall of the removable inner tube 6 by preventing distortion of the removable inner tube 6. The length of the reinforced part may be between 0.5 cm and 5 cm.

In a variation of the embodiment in depicted in FIG. 13 whereby a reinforcing tube 48 of nitenol or PEEK is attached to the outside of the removable inner tube 6 in a coaxial arrangement, the reinforcing tube 48 may be disposed with an annular ridge 51 towards or at the proximal end of the reinforcing tube 48 (FIG. 16). The ridge 51 will have a larger diameter than the proximal port 13 of the inflation coupling 12 (see below), and thus cannot pass through the proximal port 13. The annular ridge 51 will, therefore, act as a calibration stop, indicating the depth to which the removable inner tube 6 should be inserted into the medical balloon catheter 1. According to one aspect of the invention, the position of the reinforcing tube 48 disposed with an annular ridge 51 is adjustable along the length of the removable inner tube 6. According to another aspect of the invention, the position of the reinforcing tube 48 disposed with an annular ridge 51 is fixed relative to the length of the removable inner tube 6.

According to one aspect of the invention, the removable inner tube 6 is longer than the medical balloon catheter 1. A longer tube allows the inner tube 6 to protrude from the medical balloon catheter 1 when inserted in the inflation lumen 21, so that the proximal ends of the medical balloon catheter 1 and removable inner tube 6 can couple to an inflation coupling 12, and the removable inner tube 6 can couple to an afterloader. According to one aspect of the invention, the removable inner tube 6 is 3 cm, 4 cm, 5 cm, 6 cm, 7 cm, 8 cm, 9 cm, 10 cm, 11 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm longer than the medical balloon catheter 1, preferably between 5 and 15 cm longer for the esophageal application, and between 10 and 80 cm longer for the breast and the uterine applications.

According to one aspect of the invention, the kit further comprises a pusher wire 11 (FIG. 3) configured for insertion into and removal from the inflation lumen 21 to provide rigidity to the medical catheter 1 during insertion into a subject e.g. via a nasopharyngeal route, the cervical route, a skin puncture etc. The pusher wire is configured for insertion into the inflation lumen (21) to enhance the pushability of the catheter tube (5), and for removal from the inflation lumen (21) to restore the flaccidity of the catheter tube (5). A pusher wire is well known in the art, and typically comprises an elongated rod that has a high degree of flexibility and pushability, allowing it to be advanced along the desired route. The pusher wire 11 typically formed from a spring coil having a hollow centre. The pusher wire 11 is usually made from stainless steel, but can be made from Nitinol or other biocompatible materials.

According to one aspect of the invention, the kit further comprises an inflation coupling 12 (FIG. 6, 7, 8, 9) configured to couple the proximal end of the catheter tube 5 to an inflation pump 30 to allow inflation of the balloon 4. It allows, access to the open 9 proximal end 7 of the removable inner tube 6 when said removable inner tube 6 is inserted into the inflation lumen 21, during inflation.

Typically the inflation coupling 12 (FIG. 6) comprises a distal port 14, disposed with a distal seal 16, a proximal port disposed with a proximal seal 15, and a pump coupling 17, which are in fluid connection with a chamber 27 in the coupling 12. The pump coupling 17 is preferably operably connected to a valve 18.

The distal port 14 accepts the proximal end of the catheter tube 5, and can form a seal against the body of said catheter tube 5. The proximal port 13, preferably of a narrower diameter, accepts the removable inner tube 6 and can form a seal against the body of the removable inner tube 6 distal to the opening 9. The proximal port 13, may not accept the wider diameter of the catheter tube 5; a consequence is that the proximal end of the catheter end is located in the chamber 27, in fluid connection with the pump coupling 17.

When the proximal 13 and distal ports 14 are occupied, a water-tight connection is thus formed between the inflation lumen 21 of the catheter tube 5 and a pump coupling 17 for connection to an inflation pump 30 (FIG. 7). The pump coupling 17 may be a screw connection, push-fit connection, a Luer connection or other suitable coupling.

One embodiment of the invention is an inflation coupling 12 comprising:
  a distal port 14, configured to accept the proximal end of the catheter tube 5 and form a seal against the body of said catheter tube 5.
  a proximal port 13 configured to accept the removable inner tube 6 inserted in the catheter tube 5, and to form a seal against the body of the removable inner tube 6 distal to the opening 9, and
  a pump coupling 17, configured to connect to an inflation pump 30;
which ports 13, 14 and pump coupling 17 are in fluid connection with a chamber 27 in the coupling 12 which accepts the proximal end of the catheter tube 5.

Another embodiment of the invention is an inflation coupling 12 comprising:
  a distal port 14, disposed with a distal seal 16,
  a proximal port 13 disposed with a proximal seal 15, and
  pump coupling 17 operably connected with a valve;
which are in fluid connection with a chamber 27 in the coupling 12, wherein the
  distal port 14 is configured to accept the proximal end of the catheter tube 5, and to form a seal against the body of the catheter tube 5, and
  proximal port 13 is configured to accept the removable inner tube 6 and to form a seal against the body of the removable inner tube 6 distal to the opening 9, allowing the proximal end of the removable inner tube 6 to pass through the coupling 12.

The proximal 15 and distal 16 seals are preferably compressible annular rings whose inside diameter can be reduced by the application of a compression force parallel to the central axis of the ring. This might be achieved, for example, by providing a threaded extension 30, 31 of each port 13, 14 to which a bolt 25, 26 can engage (FIG. 9). Said bolt has a hollow shaft and head through which the catheter tube 1 or removable inner tube 6 can pass. Tightening the bolt 25, 26 results in compression of the respective seals 15, 16 and, a sealing of the ports 13, 14 against the wall of the removable inner tube 6 or catheter tube 1 respectively.

A central axis of the proximal port 13 and distal port 14 are preferably essentially aligned. This allows the proximal end of the inner tube 6 to pass though both ports, and to exit the inflation coupling 12. In this way, the open 9 proximal end 7 of the removable inner tube 6 extends from the inflation coupling 12, allowing access thereto for insertion of the source wire 19. According to one aspect of the invention, the inflation coupling 12, is a Y-shape coupling.

Thus, the inflation coupling 12 fluidly connects the inflation lumen 21 of the medical catheter 1 and the pump coupling 17, by forming a chamber 27 sealed by the outside surface of the catheter tube 5 at the proximal end 2 and by the outside surface of the removable inner tube 6 distal to the opening 9. The pump coupling 17 may be disposed with a valve (tap) 18 to maintain pressure in the inflation lumen 21 after the inflation pump 30 has been disconnected (FIG. 8). Thus the balloons 4, 4' remain inflated when the valve is closed.

Typically, the user inserts the tube 5 with pushing wire inside into the subject via the nasopharyngeal route, removes the pushing wire, places the inflation coupling 12 and couples the proximal end 2 of the catheter tube 5 to the distal port 14, inserts the removable inner tube 6, couples the proximal end of the removable inner tube 6 to the proximal port 13.

According to one aspect of the invention, the kit further comprises an inflation pump 30. Such a pump provides pressure of inflation fluid to the medical catheter 1 allowing gradual inflation and deflation of the balloon, and is well known in the art. Generally an inflation pump is a syringe-type arrangement, whereby the distance moved by a plunger element can be finely controlled by the practitioner and whereby the pressure applied by the fluid can be monitored by means of a pressure gauge. An embodiment of an inflation pump 30 according to the invention is depicted in FIG. 7, shown connected to the inflation coupling 12 via tubing 31. The pump 30 comprises a plunger 32 that is able to move linearly in a housing 34, changing the volume of a water-tight chamber 35 at the distal end. The chamber exits at an outlet port 36, and is fluidicly coupled to a pressure meter 37. An outlet port 36 is connected by a tubing 31 to the inflation coupling 12 (pump coupling 17). The plunger 32 is operated by a handle 33. For a fine control, the handle 33 may be turned 38 and a threaded shaft 39 of the plunger 32 advances or withdraws linearly according to the direction the handle 33 is rotated. For a coarse adjustment, the handle 33 may be pushed or pulled 39 to advance or withdraw the plunger 32 directly. The rotation or push/turning modes of operation may be selected by a button 40 on the side of the housing which controls the engagement of the thread with the housing 34. Such devices are well known in the art, for example, manufactured by Boston Scientific.

Another embodiment of the present invention is a method for delivering brachytherapy to a subject comprising:
  inserting a medical balloon catheter 1 through an entry point in the subject (e.g. a skin puncture or incision, through the nose, vagina, mouth, anus), said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;
  positioning the at least one inflatable balloon 4, 4' in the region of treatment;
  inserting a removable inner tube 6 into the inflation lumen 21 (FIG. 5) said removable inner tube 6 having an elongated body, and open 9 proximal 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

To give temporary rigidity to the medical balloon catheter 1, a pusher wire 11 (FIG. 3) will be inserted into the inflation lumen 21 (FIG. 4) of the elongated catheter tube 5 prior to advancement through the body. After the medical balloon catheter 1 has been positioned, the pusher wire 11 is removed.

Once the medical balloon catheter 1 has been fitted, the proximal end 2 can be taped onto the skin in the vicinity of the entry point. The flexibility of the elongated catheter tube 5 allows the catheter to be extensively manipulated and bent without the position of the balloons inside the body significantly changing.

The region where the medical balloon catheter 1 exits the entry point may be fixed with a plaster to the skin of the patient. This fixation secures the catheter 1 in a position between treatments, ensuring the treating portion remains at the same location with regard to the tumor area.

The method is preferably performed using a kit as defined above. The medical balloon catheter 1 may bear graduations facilitating insertion of subsequent tubes such as for esophageal or intra-uterine treatment. For example, a new medical balloon catheter 1 may be inserted each week, and remain in situ from Monday to Friday, and removed for the weekend; each new tube would be inserted on Mondays using the graduations to determine the precise depth of insertion into the oesophagus or into the uterine cavity. The treatment may continue for several weeks in a fractionated treatment. The graduations permit subsequent insertions of the medical balloon catheter 1 to the correct location each time, without the requirement for a visualisation device such as an X-ray or CT scanner.

After insertion of the medical balloon catheter 1, an inflation coupling 12 as described above may be coupled to the proximal end 2 of the catheter 1, specifically to the catheter tubing 5.

Just prior to treatment, the removable inner tube 6 is advanced along the inflation lumen 21 (FIG. 5). It is preferably advanced as far as the distal tip of the inflation lumen 21 (FIG. 5). Advantageously, the removable inner tube 6 may protrudes between 5 and 15 cm from the proximal end of the catheter tube 1, so that the proximal ends of the medical balloon catheter 1 and removable inner tube 6 can couple to an inflation coupling 12, and the removable inner tube 6 can couple to an afterloader. The outside surface of the removable inner tube 6 may be lubricated for example with a silicone, Teflon layer or with oil to assist insertion. The removable inner tube 6 may be graduated in order to warrant that the adequate length has been inserted into the medical balloon catheter 1. A region distal to the opening 9 of the removable tube 6 may be reinforced in order to ensure water-tight coupling with the inflation coupling 12, without damage to the wall of the removable tube 6. At the level of the reinforcement of the removable inner tube 6, a proximal annular ridge 51 of the reinforcing tube may warrant the removable inner tube 6 to be inserted always at the same depth.

After insertion of the removable inner tube 6, the inflation coupling 12 as described above may be coupled to the outside wall of the removable inner tube 6 distal to the opening 9. The ports 13, 14 of the inflation coupling 12 form a watertight chamber 27 so that the inflation lumen 21 can receive pressurised inflation fluid entering the chamber 27. The inflation coupling 12 also permits access to the open proximal end of the inner tube 6 allowing connection to an afterloading machine. The inflation coupling is attached to an inflation pump 30. Once inflated, the inflation coupling 12 can be sealed by a valve 18 and the pump can be removed.

The one or more balloons are inflated, typically using saline solution as inflation fluid. Saline may be mixed with 0.5 to 20% of contrast agent—such as Omnipaque—in order to allow the balloons to be viewed on X-ray pictures or CT slices The radiation source is delivered using a narrow wire 19, where a distal end is provided with a radiation-emitting substance 20 which wire is passed through the source wire lumen 22. A device known as an afterloader or afterleading machine is used to store and controllably dispense the source wire. The proximal end 7 of the inner tube 6 may be provided with an adapter allowing connection to the output end of the afterloader.

After treatment, the source wire 19 is removed, the balloons 4, 4' deflated, the inflation coupling 12 is removed and the inner tube 6 removed. The catheter 1 can remain comfortably and discretely in place for a subsequent treatment.

The same catheter 1 can remain in place for long periods without any reported discomfort or irritation, for example, up to 1, 2 or 3 weeks. According to one aspect of the invention, subsequent treatments are repeated using the same catheter 1 worn for a duration of 3 days, 5 days, 6 days, 7 days, 10 days, 2 weeks, or 3 weeks. Preferably the same catheter is worn for 5 days.

According to one aspect of the invention, a new catheter 1 is inserted at regular intervals during treatment, which may be every 2, 3, 4, 5, 6, 7, 8, 9, 10, 11, 12, 13, 14, 15, 16, 17, 18, 19, 20, or 21 days, preferably every 7 days.

According to one aspect of the invention, the radiation is administered at regular intervals during treatment, which may be every 1, 2, 3 days, preferably every day. There may be a break in administration, for example at weekends or on closed days.

Another embodiment of the present invention is a method for delivering radiotherapy to the oesophagus comprising:

inserting a medical balloon catheter 1 into the oesophagus a subject via the nasopharyngeal route, said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The insertion of the medical balloon catheter 1 can be performed using the same technique used by non-specialist to insert a feeding tube into the stomach of a subject after oral or throat surgery. The medical balloon catheter 1 is inserted via the nasopharyngeal route, i.e. through the nose and into the esophagus. Insertion is preferably carried out by a nurse, though it may equally well be carried out by the specialist. To give temporary rigidity to the medical balloon catheter 1, a pusher wire 11 (FIG. 3) will be inserted into the inflation lumen 21 (FIG. 4) of the elongated catheter tube 5 prior to advancement through the nasopharyngeal route. After the medical balloon catheter 1 has been positioned, the pusher wire 11 is removed.

Once the medical balloon catheter 1 has been fitted, the proximal end 2 can be taped, for example, behind the ear of the subject for discrete wearing until the moment for treatment. The flexibility of the elongated catheter tube 5 allows the catheter to be extensively manipulated and bent without the position of the balloons inside the esophagus significantly changing.

The region where the medical balloon catheter 1 exits the nostril is may be fixed with a plaster to the nose of the patient. This fixation secures the catheter 1 in a position between treatments, ensuring the treating portion remains at the same location with regard to the tumor area. The medical balloon catheter 1 is typically secured to the nose after insertion via the nasopharyngeal route, and between treatment sessions.

The method is preferably performed using a kit as defined above. The medical balloon catheter 1 may bear graduations facilitating insertion of subsequent tubes. For example, a new medical balloon catheter 1 may be inserted each week, and remain in situ from Monday to Friday, and removed for the weekend; each new tube would be inserted on Mondays using the graduations to determine the precise depth of insertion into the oesophagus. The treatment may continue for several weeks in a fractionated treatment. The graduations permit subsequent insertions of the medical balloon catheter 1 to the correct location each time, without the requirement for a visualisation device such as an X-ray or CT scanner.

After insertion of the medical balloon catheter 1, an inflation coupling 12 as described above may be coupled to the proximal end 2 of the catheter 1, specifically to the catheter tubing 5.

Just prior to treatment, the removable inner tube 6 is advanced along the inflation lumen 21 (FIG. 5). It is preferably advanced as far as the distal tip of the inflation lumen 21 (FIG. 5). Advantageously, the removable inner tube 6 may protrude between 5 and 15 cm from the proximal end of the catheter tube 1, so that the proximal ends of the medical balloon catheter 1 and removable inner tube 6 can couple to an inflation coupling 12, and the removable inner tube 6 can couple to an afterloader. The outside surface of the removable inner tube 6 may be lubricated for example with a silicone, Teflon layer or with oil to assist insertion. The removable inner tube 6 may be graduated in order to warrant that the adequate length has been inserted into the medical balloon catheter 1. A region distal to the opening 9 of the removable inner tube 6 may be reinforced in order to ensure water-tight coupling with the inflation coupling 12, without damage to the wall of the removable tube 6. At the level of the reinforcement of the removable inner tube 6, a proximal annular ridge 51 of the reinforcing tube may warrant the removable inner tube 6 to be inserted always at the same depth.

After insertion of the removable inner tube 6, the inflation coupling 12 as described above may be coupled to the body of the removable inner tube 6 distal to the opening 9. The ports 13, 14 of the inflation coupling 12 form a watertight chamber 27 so that the inflation lumen 21 can receive pressurised inflation fluid entering the chamber 27. The inflation coupling 12 also permits access to the open proximal end of the inner tube 6 allowing connection to an afterloader. The inflation coupling is attached to an inflation pump 30. Once inflated, the inflation coupling 12 can be sealed by a valve 18 and the pump can be removed.

The one or more balloons are inflated, typically using saline solution as inflation fluid. Saline may be mixed with 0.5 to 20% of contrast agent—such as Omnipaque—in order to allow the balloons to be viewed on X-ray pictures or CT slices The radiation source is delivered using a narrow wire 19, where a distal end is provided with a radiation-emitting substance 20 which wire is passed through the source wire lumen 22. A device known as an afterloader is used to store and controllably dispense the source wire. The proximal end 7 of the inner tube 6 may be provided with an adapter allowing connection to the output end of the afterloader.

After treatment, the source wire 19 is removed, the balloons 4, 4' deflated, the inflation coupling 12 is removed and the inner tube 6 removed. The catheter 1 can remain comfortably and discretely in place for a subsequent treatment.

The same catheter 1 can remain in place for long periods without any reported discomfort or irritation, for example, up to 1, 2 or 3 weeks. According to one aspect of the invention, subsequent treatments are repeated using the same catheter 1 worn for a duration of 3 days, 5 days, 6 days, 7 days, 10 days, 2 weeks, or 3 weeks. Preferably the same catheter is worn for 5 days.

According to one aspect of the invention, a new catheter 1 is inserted at regular intervals during treatment, which may be every 2, 3, 4, 5, 6, 7, 8, 9, 10, 11, 12, 13, 14, 15, 16, 17, 18, 19, 20, or 21 days, preferably every 7 days.

According to one aspect of the invention, the radiation is administered at regular intervals during treatment, which may be every 1, 2, 3 days, preferably every day. There may be a break in administration, for example at weekends or on closed days.

Another embodiment of the present invention is a method for delivering radiotherapy to the internal walls of the uterus comprising:

inserting a medical balloon catheter 1 into the uterus of a subject via the cervical route, said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The insertion of the medical balloon catheter 1 can be performed using the same technique used by non-specialist to insert a hysterometer inside the uterine cavity. The medical balloon catheter 1 is inserted via the cervix uteri, i.e. through the vagina to the uterine cavity. Insertion is preferably carried out by a radiation oncologist, though it may equally well be carried out by the gynecologist. To give temporary rigidity to the medical balloon catheter 1, a pusher wire 11 (FIG. 3) will be inserted into the inflation lumen 21 (FIG. 4) of the elongated catheter tube 5 prior to advancement through the cervical route. After the medical balloon catheter 1 has been positioned, the pusher wire 11 is removed.

Catheter 5 may be fixed at the exit of the cervix in order to secure the maintenance of catheter 1 inside the uterine space.

Once the medical balloon catheter 1 has been fitted and the proximal end has fixed to the perineum using a plaster, the proximal end 2 can be taped, for example, on the skin on the side of the vagina for atraumatic wearing until the moment for treatment. The flexibility of the elongated catheter tube 5 allows the catheter to be extensively manipulated and bent without the position of the balloons inside the uterus significantly changing.

The region where the medical balloon catheter 1 exits the vagina may be fixed with a plaster to the perineal skin of the patient. This fixation secures the catheter 1 in a position between treatments, ensuring the treating portion remains at the same location with regard to the tumor area. The medical balloon catheter 1 is typically secured to the skin after insertion via the cervical route, and between treatment sessions.

The method is preferably performed using a kit as defined above. Medical balloon catheter 1 may bear graduations facilitating insertion of subsequent tubes. For example, a new medical balloon catheter 1 may be inserted each week, and remain in situ from Monday to Friday, and removed for the weekend; each new tube would be inserted on Mondays using the graduations to determine the precise depth of insertion into the uterine cavity. The treatment may continue for several weeks in a fractionated treatment. The graduations permit subsequent insertions of the medical balloon catheter 1 to the correct location each time, without the requirement for a visualisation device such as an X-ray or CT scanner.

After insertion of the medical balloon catheter 1, an inflation coupling 12 as described above may be coupled to the proximal end 2 of the catheter 1, specifically to the catheter tubing 5.

Just prior to treatment, the removable inner tube 6 is advanced along the inflation lumen 21 (FIG. 5). It is preferably advanced as far as the distal tip of the inflation lumen 21 (FIG. 5). Advantageously, the removable inner tube 6 may protrude between 10 and 80 cm from the proximal end of the catheter tube 1, so that the proximal ends of the medical balloon catheter 1 and removable inner tube 6 can couple to an inflation coupling 12, and the removable inner tube 6 can couple to an afterloader. The outside surface of the removable inner tube 6 may be lubricated for example with a silicone, Teflon layer or with oil to assist insertion. The removable inner tube 6 may be graduated in order to warrant that the adequate length has been inserted into the medical balloon catheter 1. A region distal to the opening 9 of the removable tube 6 may be reinforced in order to ensure water-tight coupling with the inflation coupling 12, without damage to the wall of the removable tube 6. At the level of the reinforcement of the removable inner tube 6, a proximal annular ridge 51 of the reinforcing tube may warrant the removable inner tube 6 to be inserted always at the same depth.

After insertion of the removable inner tube 6, the inflation coupling 12 as described above may be coupled to the body of the removable inner tube 6 distal to the opening 9. The ports 13, 14 of the inflation coupling 12 form a watertight chamber 27 so that the inflation lumen 21 can receive pressurised inflation fluid entering the chamber 27. The inflation coupling 12 also permits access to the open proximal end of the inner tube 6 allowing connection to an afterloader. The inflation coupling is attached to an inflation pump 30. Once inflated, the inflation coupling 12 can be sealed by a valve 18 and the pump can be removed.

The one or more balloons are inflated, typically using saline solution as inflation fluid. Saline may be mixed with 0.5 to 20% of contrast agent—such as Omnipaque 300 (Nycomed)—in order to allow the balloons to be viewed on X-ray pictures or CT slices The radiation source is delivered using a narrow wire 19, where a distal end is provided with a radiation-emitting substance 20 which wire is passed through the source wire lumen 22. A device known as an afterloader is used to store and controllably dispense the source wire. The proximal end 7 of the inner tube 6 may be provided with an adapter allowing connection to the output end of the afterloader.

After treatment, the source wire 19 is removed, the balloons 4, 4' deflated, the inflation coupling 12 is removed and the inner tube 6 removed. The catheter 1 can remain comfortably and discretely in place for a subsequent treatment.

The same catheter 1 can remain in place for long periods without any reported discomfort or irritation, for example, up to 1, 2 or 3 weeks. According to one aspect of the invention, subsequent treatments are repeated using the same catheter 1 worn for a duration of 3 days, 5 days, 6 days, 7 days, 10 days, 2 weeks, or 3 weeks. Preferably the same catheter is worn for 5 days.

According to one aspect of the invention, a new catheter 1 is inserted at regular intervals during treatment, which may be every 2, 3, 4, 5, 6, 7, 8, 9, 10, 11, 12, 13, 14, 15, 16, 17, 18, 19, 20, or 21 days, preferably every 7 days.

According to one aspect of the invention, the radiation is administered at regular intervals during treatment, which may be every 1, 2, 3 days, preferably every day. There may be a break in administration, for example at weekends or on closed days.

Another embodiment of the present invention is a method for delivering radiotherapy to a breast resection cavity comprising:

inserting a medical balloon catheter 1 into a breast resection cavity of a subject after a breast tumor has been removed (breast conserving surgery), said medical balloon catheter 1 having a proximal 2 end and distal 3 end, comprising an elongated catheter tube 5 with an inflation lumen 20 extending therewithin and at least one inflatable balloon 4, 4' towards the distal end 3 in fluid communication with the catheter tube 5 inflation lumen 21, wherein the inflation lumen 21 is configured to carry inflation fluid to the least one inflatable balloon 4, 4' in the presence of the removable inner tube 6;

positioning the at least one inflatable balloon 4, 4' in the region of treatment;

inserting a removable inner tube 6 into the inflation lumen 21 (FIG. 5) said removable inner tube 6 having an elongated body, and open 9 proximal 7, a closed 10 distal end 8 and a source wire lumen 22 extending therewithin, said removable inner tube 6 configured for insertion into and removal from at least part of the length of the inflation lumen 21, source wire lumen 22 configured to receive a source wire 19 bearing a therapeutic radiation source 20;

inflating the at least one inflatable balloon 4, 4' (FIG. 7);

advancing a radiation source wire 19 though the source wire lumen 22 to the region of treatment, and administering a radiation dose (FIG. 8);

removing the radiation source wire 19;

deflating the at least one inflatable balloon 4, 4';

withdrawing the removable inner tube 6; and optionally leaving the medical balloon catheter 1 in situ for a subsequent treatment session.

The method is preferably performed using a kit as defined above. The insertion of the medical balloon catheter 1 can be performed either during the surgical tumor resection or later, using ultra-sound or another imaging technique to position the balloon inside the tumor resection cavity after puncturing the skin with a trocard needle. The medical balloon catheter 1 is inserted via surgical scar or through the skin. To give temporary rigidity to the medical balloon catheter 1, a pusher wire 11 (FIG. 3) or a mandrel will be inserted into the inflation lumen 21 (FIG. 4) of the elongated catheter tube 5 prior to insertion. After the medical balloon catheter 1 has been positioned, the pusher wire 11 is removed.

Once the medical balloon catheter 1 has been fitted and the proximal end has fixed to the breast skin using a plaster, the proximal end 2 which exits the breast can be taped on the breast of the subject for atraumatic wearing until the moment for treatment. The flexibility of the elongated catheter tube 5 allows the catheter to be extensively manipulated and bent without the position of the balloons inside the breast cavity significantly changing.

The region where the medical balloon catheter 1 exits the breast may be fixed with a plaster to the skin of the patient. This fixation secures the catheter 1 in a position between treatments, ensuring the treating portion remains at the same location with regard to the tumor area. The medical balloon catheter 1 is typically secured to the skin of the breast after insertion and between treatment sessions.

After insertion of the medical balloon catheter 1, an inflation coupling 12 as described above may be coupled to the proximal end 2 of the catheter 1, specifically to the catheter tubing 5.

Just prior to treatment, the removable inner tube 6 is advanced along the inflation lumen 21 (FIG. 5). It is preferably advanced as far as the distal tip of the inflation lumen 21 (FIG. 5). Advantageously, the removable inner tube 6 may protrude between 10 and 80 cm from the proximal end of the catheter tube 1, so that the proximal ends of the medical balloon catheter 1 and removable inner tube 6 can couple to an inflation coupling 12, and the removable inner tube 6 can couple to an afterloader. The outside surface of the removable inner tube 6 may be lubricated for example with a silicone, Teflon layer or with oil to assist insertion. The removable inner tube 6 may be graduated in order to warrant that the adequate length has been inserted into the medical balloon catheter 1. A region distal to the opening 9 of the removable tube 6 may be reinforced in order to ensure water-tight coupling with the inflation coupling 12, without damage to the wall of the removable tube 6. At the level of the reinforcement of the removable inner tube 6, a proximal annular ridge 51 of the reinforcing tube may warrant the removable inner tube 6 to be inserted always at the same depth.

After insertion of the removable inner tube 6, the inflation coupling 12 as described above may be coupled to the body of the removable inner tube 6 distal to the opening 9. The ports 13, 14 of the inflation coupling 12 form a watertight chamber 27 so that the inflation lumen 21 can receive pressurised inflation fluid entering the chamber 27. The inflation coupling 12 also permits access to the open proximal end of the inner tube 6 allowing connection to an afterloader. The inflation coupling is attached to an inflation pump 30. Once inflated, the inflation coupling 12 can be sealed by a valve 18 and the pump can be removed.

The one or more balloons are inflated, typically using saline solution as inflation fluid. Saline may be mixed with 0.5 to 20% of contrast agent such as Omnipaque—in order to allow the balloons to be viewed on X-ray pictures or CT slices The radiation source is delivered using a narrow wire 19, where a distal end is provided with a radiation-emitting substance 20 which wire is passed through the source wire lumen 22. A device known as an afterloader is used to store and controllably dispense the source wire. The proximal end 7 of the inner tube 6 may be provided with an adapter allowing connection to the output end of the afterloader.

After treatment, the source wire 19 is removed, the balloons 4, 4' deflated, the inflation coupling 12 is removed and the inner tube 6 removed. The catheter 1 can remain comfortably and discretely in place for a subsequent treatment.

The same catheter 1 can remain in place for long periods without any reported discomfort or irritation, for example, up to 1, 2 or 3 weeks. According to one aspect of the invention, subsequent treatments are repeated using the same catheter 1 worn for a duration of 3 days, 5 days, 6 days, 7 days, 10 days, 2 weeks, or 3 weeks. Preferably the same catheter is worn for 5 days.

According to one aspect of the invention, the radiation is administered at regular intervals during treatment, which may be every 1, 2, 3 days, preferably every day. There may be a break in administration, for example at weekends or on closed days.

As described herein, the kit and method delivers a suitable dosage of radiation to the region of treatment, for example, oesophageal or uterine lumen, or to a breast resection cavity and is configured to provide the dosage over at regular intervals if necessary. Single high doses or fractionated repeated low doses may be delivered as the catheter 1 allows multiple treatments to be performed.

For curative treatments, it is preferred that a low dose of radiation, in the order of about 2 up to about 4 Gray (Gy) per fraction prescribed at the periphery of the esophagus as seen on CT slices be the typical radiation dose provided to treat cancerous cells. Preferably, 2 to 3 Gy per fraction will provide a proper dosage level for a curative treatment, allowing efficacy and preventing complications such as esophageal stenosis (late side effect). The treatment could be prescribed as a boost after external radiotherapy (50 Gy) combined with chemotherapy (taxotere and cisplatin), adding 10 to 20 Gy of brachytherapy during 1 to 2 weeks.

For uterine tumors, dose fractions of 3 to 6 Gy, one to three times a week for total doses up to 50 to 60 Gy are considered to be sufficient for curative treatments. Lower total doses may be delivered when patients receive a combination of external radiotherapy and brachytherapy; for instance 40 Gy of external radiotherapy combined with 3 to 4 times 5 to 6 Gy of intra-uterine brachytherapy.

For breast cancer patients, total doses of 30 Gy delivered in 5 consecutive fractions of 6 Gy, prescribed at 1 cm from the balloon surface could be sufficient for partial breast radiotherapy. For boost treatments, a dose of 3 times 5 Gy combined with 40 to 50 Gy of external breast radiotherapy should be equivalent to the efficacy of standard electron boost delivered by external radiotherapy.

In esophageal cancers, fractionated brachytherapy could also be prescribed as a preoperative therapy in order to increase the local effect of chemotherapy and radiation and to increase the number of complete responders, as it is shown that complete responders (to radio-chemotherapy) are the only ones to survive esophageal cancer.

For palliative treatments, a dose of 5 Gy could be prescribed on the outer surface of the esophagus (as seen on CT slices) 1 to 3 times per week, for 1 to several weeks to a total dose of 10 to 30 Gy. The same range of doses could be delivered to patients presenting with a uterine cancer in a palliative situation.

The radiation delivered to the oesophageal wall on a length of 10 cm using a 1.3 cm balloon diameter should be in the range from about 2 to 3 Gy and is usually not delivered in less than thirty seconds, but in 1 minute, 1.5 minutes, 2 minutes, 2.5 minutes, 3 minutes, 3.5 minutes, 4 minutes, 4.5 minutes, or 5 minutes, or for a period between any two of the aforementioned values, preferably between 2 to 5 minutes.

The same range of duration is standard for uterine and breast cancer treatments.

It is contemplated that different radiation sources be used, and the preferred radiation sources include iridium[192] if gamma radiation is used, and californium[252] if neutron particles are used. Further, it is contemplated that the radiation sources may provide neutron particles or gamma rays to affect the target cells. The use of gamma or neutron emitting radiation sources is well known for treating and killing cancerous cells.

Other modifications can be made to the present invention without departing from the spirit and scope thereof. The specific dimensions, doses, times and materials of constructions are provided as examples and substitutes are readily contemplated which do not depart from the invention.

EXAMPLES

The invention is illustrated by way of the following non-limiting examples.

1. Brachytherapy of the Oesophageal Lumen

A 65 y old patient presented with an inoperable esophageal cancer. The patient could not be operated because of high risk of anesthesy. The tumor, an epidermoid cancer, was located at the inner-lower third level in the esophagus and was 8 cm long. The esophageal wall thickness, as seen on the CT slices, was up to 1 cm thick in some areas.

As the patient was in bad general state, a palliative therapy was chosen. The patient received first 30 Gy of external radiotherapy in 10 sessions of 3 Gy.

One week later, a nasopharyngeal access catheter was inserted by the nurse of the radiation oncology department. The treating part of the catheters with the deflated balloons was placed approximately in regard to the cancer area. A connector with 2 valve systems was tightly fixed on the proximal end of the access catheter. A catheter allowing for radioactive source introduction was introduced inside the access catheter. Before introducing the source catheter, a few drops of oil were dripped on the distal part of the source catheter, on 5 to 10 cm of the distal length.

The inner catheter allowing for radioactive source introduction was pushed inside the access catheter until the tip of the access catheter was reached (the source catheter blocked against the tip of the access catheter).

The proximal and distal valves of the coupling system was secured until the whole coupling system became water-tight.

A syringe with a manometer with 20 cc of a mixture of 2 cc of Omnipaque and 18 cc of saline was connected to the balloon system.

A coronal view was made using a CT scanner. This view allowed the position of the deflated balloon to be adapted, seen with the peripheral platinum markers, to the position of the tumor as seen on CT scan slices. The position was adapted to cover the tumor length (8 cm) and to keep an equal margin from both sides of the tumor in regard to the length of the balloon.

Once the position was defined and satisfactory, the balloon was inflated with 20 cc of the saline-omnipaque mixture which led to an inflation diameter of the balloon of 14 mm. Jointed CT slices were made on the whole length of the esophageal tumor.

The tumor outer surface was drawn on the screen of the CT using a special brachytherapy program (Plato dosimetric program by Nucletron, for instance).

A dose of 5 Gy was delivered during each brachytherapy session, 1 to 2 times a week. After 2 weeks, a total dose of 20 Gy has been delivered in 4 fractions. The patient felt perfectly well and tolerated the treatment very easily. The inflation time of the balloon system was in the range of 8 minutes per treatment to deliver 5 Gy. This was slightly too long. The patient did not feel well after approximately 5 minutes, at each treatment session. He reported a pain in the oesophageal area. The radiation treatment was interrupted, the source was withdrawn and the balloon was deflated in a few seconds. After 10 minutes of interruption, the patient was feeling better, the balloon was reinflated and the radioactive source was repositioned automatically at the place where the treatment had been interrupted. Radiation therapy was perfectly delivered according to dose prescription.

The patient was observed for the following months to detect any complication due to brachytherapy. The still patient felt well 3 months at the end of brachytherapy, and to date remains under follow-up. The tumor has shrunk, no late side effect (strictures) has been seen, and the patient is eating normally.

2. Brachytherapy of the Uterine Cavity

A 90 y old lady presented with an endometrial cancer. She had been bleeding regularly for 2 years and it was decided at that time to wait and see whether the patient, who was in a poor medical status with many other pathologies, would survive long enough to suffer from tumor progress.

One day the patient complained of severe vaginal bleeding. The hemogram showed an haemoglobin level of 7 gr. The patient was feeling very weak and was taken to hospital.

The surgeons refused to perform an intervention (uterus ablation or hysterectomy) because of the poor general status and the high anesthaetic risk.

After debating, it was proposed to perform a hypofractionated therapy using external radiotherapy and brachytherapy. The patient received 2 courses of 6 Gy external radiotherapy (4 field technique) that encompassed the whole uterus as seen on simulation CT scan slices, one week apart. She also benefited from 4 brachytherapy sessions of 6 Gy prescribed at the peripheral surface of the uterus as seen on simulation CT scan slices using a balloon catheter.

The treatment was very well tolerated. After 6 months, the patient still did not bleed and did not require a surgical intervention. To date, she is kept under follow-up.

3. Brachytherapy of the Breast

A 70 y old lady presenting with a 1 cm diameter ductal carcinoma in the lower external quadrant of the right breast benefits from a sentinel lymphnode technique. The anapathological examination does not show any invaded lymphnode.

The breast tumor is resected with a security margin of a least 1 cm from all sides (quadantectomy). The pathological examination shows a grade 1 tumor and confirms the negativity of the lymphatic invasion.

Catheter 1 is introduced inside the resection cavity one week after the intervention under ultrasonographic guidance, using a trocard needle.

Inner catheter 6 is introduced and the coupling device is secured around proximal ends of catheters 1 and 6. Balloon inflation is done up to a diameter of 4 cm. Images are made under CT scan which show the adequate position of the system and a tight contact of the balloon with the resection cavity walls.

A radiation dose of 6 Gy is prescribed and delivered at a distance of 1 cm from the surface of the balloon. The balloon is deflated and the coupling device is removed. This treatment takes place every day for five consecutive days and allows prescribing 30 Gy on the high risk area around the resection cavity. After five days, catheter 1 is removed.

The patient does not need any external radiation therapy and spares five weeks of standard therapy (external radiotherapy). She comes back regularly for controls. Two years later no local recurrence is detected on CT slices.

The invention claimed is:

1. A kit for delivering brachytherapy to a subject comprising: a medical balloon catheter comprising: a catheter tube having a proximal end and a closed distal end, and an elongated body with a single lumen that is an inflation lumen extending therewithin, and at least one inflatable balloon towards the distal end in fluid communication with the inflation lumen, wherein the inflation lumen is configured to slidably receive a removable inner tube along substantially its entire length, and wherein the catheter tube is configured such that in a folded condition a kink is generated at a position on the tube, wherein the kink, when the catheter tube is unfolded while inserted in the subject, is removed such that the inflation lumen can slidably receive a removable inner tube that advances past the position where the kink was generated, the inflation lumen configured to carry inflation fluid to the at least one inflatable balloon when the removable inner tube is present in the inflation lumen; and a removable inner tube having an elongated body, an open proximal end, a closed distal end, and a source wire lumen extending therewithin, wherein the removable inner tube is configured for insertion into and removal from substantially the entire length of the inflation lumen, and the source wire lumen configured to receive a source wire bearing a therapeutic radiation source.

2. Kit according to claim 1, further comprising an inflation coupling configured to couple the proximal end of the catheter tube to an inflation pump to allow inflation of the balloon and access to the open proximal end of the removable inner tube when said removable inner tube is inserted into the inflation lumen, during inflation.

3. Kit according to claim 2, wherein said inflation coupling comprises:
    a distal port, disposed with a distal seal,
    a proximal port disposed with a proximal seal, and
    a pump coupling operably connected to a valve,
    wherein said ports and pump coupling are in fluid connection with a chamber in the inflation coupling,
    wherein the distal port is configured to accept the proximal end of the catheter tube, and to form a seal against the body of the catheter tube, and the proximal port is configured to accept the removable inner tube and to form a seal against the body of the removable inner tube distal to the opening end, allowing the proximal end of the removable inner tube to pass through the inflation coupling.

4. Kit according to claim 1, wherein an outer diameter of the catheter tube is between 2 mm and 6 mm.

5. Kit according to claim 1, wherein the catheter tube has a flexural rigidity that is less than that of the removable inner tube.

6. Kit according to claim 1, wherein the catheter tube is made from polyrurethane or a polyurethane-containing compound.

7. Kit according to claim 1, wherein the inflation lumen has a diameter between 5% and 20% greater than an outer diameter of the removable inner tube.

8. Kit according to claim 1 wherein the catheter tube is disposed with a non-distensible cord between its proximal and distal ends which prevents longitudinal distension of the medical catheter.

9. Kit according to claim 8, wherein the cord is disposed within, outside or inside a wall of the catheter tube.

10. Kit according to claim 1, wherein the proximal end of the catheter tube is reinforced to reduce deformation by application of circumferential pressure.

11. Kit according to claim 10, wherein said reinforcement comprises
    an outer tube disposed over the proximal end of the catheter tube;
    an inner tube inserted into the proximal end of the catheter tube; or
    an extension to the proximal end of the catheter tube.

12. Kit according to claim 1, wherein the medical catheter comprises visible graduations marked at least partly along a length of the catheter tube.

13. Kit according to claim 1, wherein the removable inner tube has a wall having a thickness of between 0.1 mm and 0.4 mm.

14. Kit according to claim 1, wherein the removable inner tube has a flexural rigidity that is greater than that of the catheter tube.

15. Kit according to claim 1, wherein the proximal end of the removable inner tube is reinforced to reduce deformation by application of circumferential pressure.

16. Kit according to claim 15, wherein said reinforcement comprises
    a reinforcing outer tube disposed over the removable inner tube at or towards the proximal end of the removable inner tube;
    a reinforcing inner tube inserted into the removable inner tube at or towards the proximal end of the removable inner tube; or
    a reinforcing extension to the proximal end of the removable inner tube.

17. Kit according to claim 16, where the reinforcing outer tube disposed over the removable inner tube, is disposed with an annular ridge at or towards a proximal end of the reinforcing tube.

18. Kit according to claim 1, wherein the removable inner tube comprises visible graduations marked at least partly along its length.

19. Kit according to claim 1 wherein a flexural rigidity of the removable inner tube is between 1% and 60% greater than that of the catheter tube.

20. Kit according to claim 1, wherein the removable inner tube is made of polyimide, PEEK (polyetheretherketone) or polyethylene.

21. Kit according to claim 1, wherein the diameter of the source wire lumen of the removable inner tube is between 0.5 mm and 1.9 mm.

22. Kit according to claim 1, wherein the removable inner tube is between 3 and 90 cm longer than the medical balloon catheter.

23. Kit according to claim 1, further comprising a removable pusher wire configured for insertion into and removal from the inflation lumen to provide rigidity to the catheter tube during insertion into the subject via a nasopharyngeal route.

24. Kit according to claim 23, wherein said pusher wire has a flexural rigidity that is greater than that of the removable inner tube.

25. Kit according to claim 1, further comprising an inflation pump.

26. Kit according to claim 1, where the medical balloon catheter is configured for insertion into the oesophagus via a nasopharyngeal route.

27. Kit according to claim 1, where the medical balloon catheter is configured for insertion into the uterine cavity via a cervical route.

28. Kit according to claim 1, where the medical balloon catheter is configured for insertion into breast tissue of a breast via an incision or needle puncture in the breast.

* * * * *